(12) United States Patent
Shin et al.

(10) Patent No.: US 12,101,984 B2
(45) Date of Patent: Sep. 24, 2024

(54) DISPLAY DEVICE

(71) Applicants: SAMSUNG DISPLAY CO., LTD., Yongin-si (KR); Pusan National University Industry-University Cooperation Foundation, Busan (KR)

(72) Inventors: Hosik Shin, Yongin-si (KR); Jinwoo Oh, Busan (KR); Eunjung Choi, Busan (KR); Jaemin Shin, Yongin-si (KR); Jiwon Lee, Yongin-si (KR); Jangyeol Yoon, Yongin-si (KR)

(73) Assignees: SAMSUNG DISPLAY CO., LTD., Gyeonggi-Do (KR); PUSAN NATIONAL UNIVERSITY INDUSTRY UNIVERSITY COOPERATION FOUNDATION, Busan (KR)

( * ) Notice: Subject to any disclaimer, the term of this patent is extended or adjusted under 35 U.S.C. 154(b) by 127 days.

(21) Appl. No.: 17/545,126

(22) Filed: Dec. 8, 2021

(65) Prior Publication Data

US 2022/0302226 A1    Sep. 22, 2022

(30) Foreign Application Priority Data

Mar. 18, 2021    (KR) .................. 10-2021-0035488

(51) Int. Cl.
*H10K 59/60*    (2023.01)
*H10K 59/122*    (2023.01)

(52) U.S. Cl.
CPC ........... *H10K 59/60* (2023.02); *H10K 59/122* (2023.02)

(58) Field of Classification Search
CPC ...... G01N 21/78; H10K 59/60; H10K 59/122; H10K 59/00; A61B 5/6824; A61B 5/6833; A61B 5/681; A61B 5/1455; A61B 5/6898
See application file for complete search history.

(56) References Cited

U.S. PATENT DOCUMENTS

| | | |
|---|---|---|
| 9,477,339 B2 | 10/2016 | Hyun |
| 2009/0281394 A1 | 11/2009 | Russell et al. |
| 2011/0158653 A1 | 6/2011 | Mazed |
| 2013/0230464 A1* | 9/2013 | Yi ..................... A61K 49/0056 435/7.37 |
| 2014/0142459 A1 | 5/2014 | Jayalth et al. |
| 2017/0035354 A1 | 2/2017 | Jayalath et al. |

(Continued)

FOREIGN PATENT DOCUMENTS

| | | |
|---|---|---|
| KR | 1020160032294 A | 3/2016 |
| KR | 101825821 B1 | 3/2018 |
| KR | 102161573 B1 | 10/2020 |

*Primary Examiner* — Vongsavanh Sengdara
(74) *Attorney, Agent, or Firm* — CANTOR COLBURN LLP

(57) ABSTRACT

A display device includes: a display panel including a sensor area and a display area, where the display panel includes an upper surface and a lower surface opposite to the upper surface; and a discoloration sensor layer overlapping the sensor area, where discoloration sensor layer is disposed on one of the upper surface of the display panel and the lower surface of the display panel, and discolored when exposed to a target material. A first through portion is defined through the display panel from the upper surface to the lower surface of the display panel, and the discoloration sensor layer overlaps the first through portion.

19 Claims, 19 Drawing Sheets

(56) References Cited

U.S. PATENT DOCUMENTS

| | | | |
|---|---|---|---|
| 2020/0310210 A1* | 10/2020 | Zhang | H10K 59/50 |
| 2020/0328377 A1* | 10/2020 | Seo | H10K 59/00 |
| 2020/0411625 A1* | 12/2020 | Seo | G02F 1/13452 |
| 2021/0028252 A1* | 1/2021 | Hong | H10K 59/00 |
| 2021/0036070 A1* | 2/2021 | Jeon | H10K 59/60 |

* cited by examiner

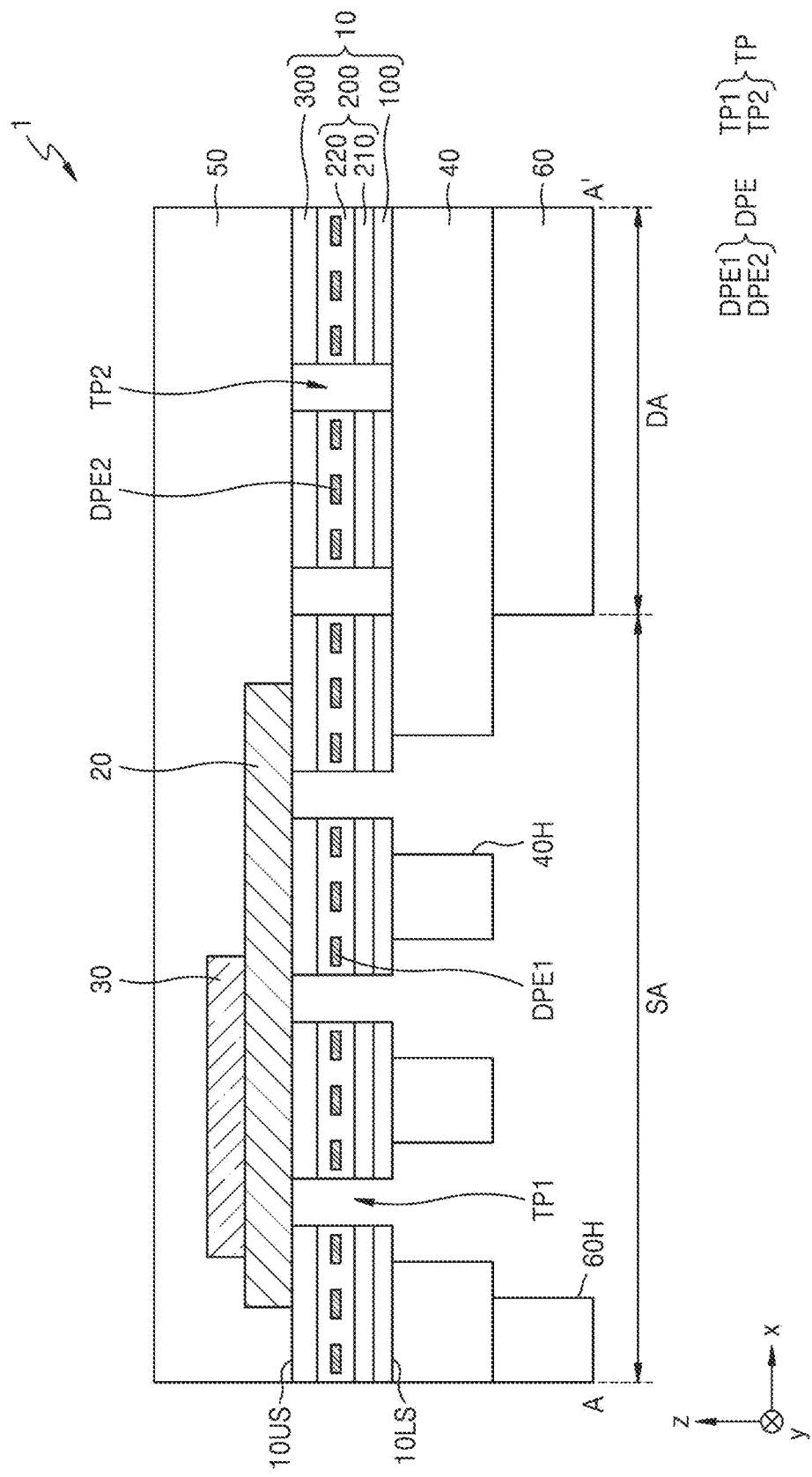

DISPLAY DEVICE

This application claims priority to Korean Patent Application No. 10-2021-0035488, filed on Mar. 18, 2021, and all the benefits accruing therefrom under 35 U.S.C. § 119, the content of which in its entirety is herein incorporated by reference.

BACKGROUND

1. Field

One or more embodiments relate to a display device, and more particularly, to a display device capable of sensing a target material.

2. Description of the Related Art

Mobile electronic devices have been widely used. Recently, tablet personal computers ("PC"s) have been widely used as mobile electronic devices, in addition to small electronic devices such as mobile phones. Such electronic devices may include a display device having various functions, for example, providing visual information, such as an image or a video, to a user.

Recently, flexible display devices that are bendable, foldable, or rollable have been researched and developed. Further, there has been an active research and development of stretchable display devices that may be changed to various shapes.

In addition, devices including a sensor capable of diagnosing various illnesses has been developed. The sensor may include, for example, a discoloration sensor that is discolored when exposed to a target material, and the presence or absence of the target material may be identified by checking the discoloration. Alternatively, the sensor may include a sensor circuit that varies in resistance when exposed to a target material.

SUMMARY

One or more embodiments include a display device that detects a target material and displays the detection result, to diagnose various illnesses.

According to an embodiment, a display device includes a display panel including a sensor area and a display area, wherein the display panel includes an upper surface and a lower surface opposite to the upper surface, and a discoloration sensor layer overlapping the sensor area, where the discoloration sensor layer is disposed on one of the upper surface of the display panel and the lower surface of the display panel, and discolored when exposed to a target material. In such an embodiment, a first through portion is defined through the display panel from the upper surface to the lower surface of the display panel, and the discoloration sensor layer overlaps the first through portion.

In an embodiment, the discoloration sensor layer may include M13 bacteriophage.

In an embodiment, the display device may further include a light detection layer overlapping the sensor area, where the light detection layer may include a photodiode and a color filter disposed on the photodiode, the discoloration sensor layer may be arranged between the light detection layer and the display panel, and the color filter may be arranged between the display panel and the photodiode.

In an embodiment, the display device may further include a lower cover facing the lower surface of the display panel, where a lower hole may be defined in the lower cover to the first through portion, and the lower hole may expose the discoloration sensor layer.

In an embodiment, the lower cover may include an elastomer.

In an embodiment, the discoloration sensor layer may face the upper surface of the display panel.

In an embodiment, the discoloration sensor layer may be arranged between the display panel and the lower cover.

In an embodiment, the display panel may include a substrate, a display layer disposed on the substrate, and a light reflection layer disposed on the display layer, and the light reflection layer may overlap the sensor area.

In an embodiment, the display panel may further include a substrate, and a display layer disposed on the substrate, where the display layer may include a first display element overlapping the sensor area and a second display element overlapping the display area.

In an embodiment, a second through portion may be defined through the display panel from the upper surface to the lower surface, and the second through portion may overlap the display area.

According to another embodiment, a display device includes a display panel including a sensor area and a display area, where the display panel includes an upper surface and a lower surface opposite to the upper surface, and an M13 bacteriophage overlapping the sensor area. In such an embodiment, a first through portion is defined through the display panel from the upper surface to the lower surface, and overlaps the sensor area.

In an embodiment, the display device may further include a discoloration sensor layer overlapping the sensor area, where the discoloration sensor layer may be disposed on one of the upper surface of the display panel and the lower surface of the display panel, and discolored when exposed to a target material, and the M13 bacteriophage may be arranged in the discoloration sensor layer.

In an embodiment, the display device may further include a light detection layer overlapping the sensor area, where the light detection layer may include a photodiode and a color filter disposed on the photodiode, the discoloration sensor layer may be arranged between the light detection layer and the display panel, and the color filter may be arranged between the display panel and the photodiode.

In an embodiment, the display device may further include a lower cover facing the lower surface of the display panel, where a lower hole may be defined through the lower cover to overlap the first through portion, and the lower hole may expose the discoloration sensor layer.

In an embodiment, the lower cover may include an elastomer.

In an embodiment, the discoloration sensor layer may face the upper surface of the display panel.

In an embodiment, the discoloration sensor layer may be arranged between the display panel and the lower cover, the display panel may include a substrate, a display layer disposed on the substrate, and a light reflection layer disposed on the display layer, and the light reflection layer may overlap the sensor area.

In an embodiment, the display panel further may further include a substrate, and a display layer disposed on the substrate, where the display layer may include a first display element overlapping the sensor area and a second display element overlapping the display area.

In an embodiment, the display panel may further include a substrate, and a sensor circuit layer disposed on the substrate to overlap the sensor area, where the sensor circuit layer may include a sensor thin-film transistor and a resistance of the sensor thin-film transistor may vary when exposed to a target material, and the sensor thin-film transistor may include a semiconductor layer on which the M13 bacteriophage is arranged.

In an embodiment, a second through portion may be defined through the display panel from the upper surface to the lower surface, and the second through portion may overlap the display area.

BRIEF DESCRIPTION OF THE DRAWINGS

The above and other features of embodiments of the invention will be more apparent from the following description taken in conjunction with the accompanying drawings, in which:

FIG. 2 is a cross-sectional view schematically illustrating a display device according to an embodiment;

DETAILED DESCRIPTION

Figure 1A:
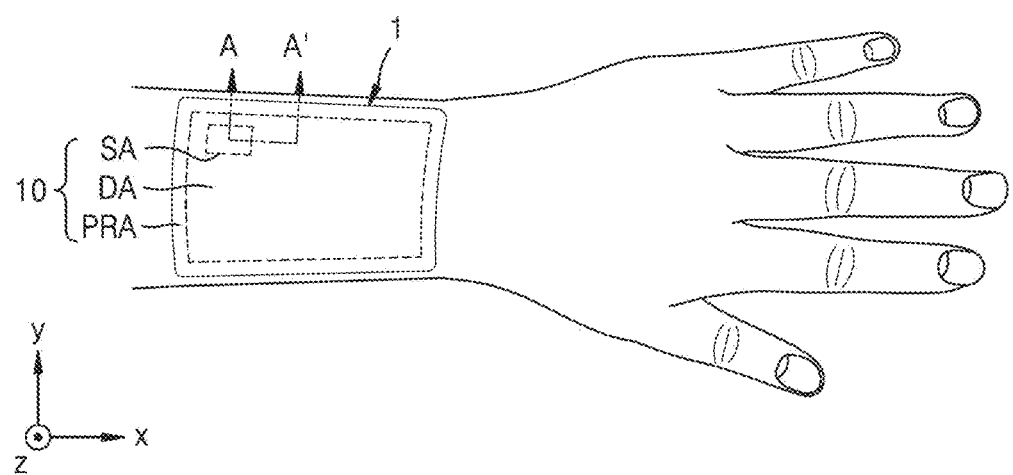
FIGS. 1A to 1C are views schematically illustrating a display device according to various embodiments.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a", "an," "the," and "at least one" do not denote a limitation of quantity, and are intended to include both the singular and plural, unless the context clearly indicates otherwise. For example, "an element" has the same meaning as "at least one element," unless the context clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

When an embodiment may be implemented differently, a certain process order may be performed differently from the described order. For example, two consecutively described processes may be performed substantially at the same time or performed in an order opposite to the described order.

It will be understood that when a layer, region, or component is referred to as being connected to another layer, region, or component, it can be directly or indirectly connected to the other layer, region, or component. That is, for example, intervening layers, regions, or components may be present. For example, when layers, areas, or elements or the like are referred to as being "electrically connected," they may be directly electrically connected, or layers, areas or elements may be indirectly electrically connected, and an intervening layer, region, component, or the like may be present therebetween.

A display device displays a moving image or a still image, and may be used not only in portable electronic devices such as mobile phones, smartphones, tablet personal computers ("PC"s), mobile communication terminals, electronic notebooks, electronic books, portable multimedia players ("PMP"s), navigation, and ultra-mobile PCs ("UMPC"s), but also as a display screen of various products such as televisions, laptops, monitors, billboards, Internet of things ("IoT"), or the like. In addition, a display device according to an embodiment may be used in wearable devices such as smart watches, watch phones, goggle-type displays, and head-mounted displays ("HMD"s). In addition, the display device according to an embodiment may be used in instrument panels for automobiles, center information displays ("CID"s) arranged on a center fascia or a dashboard of automobiles, room mirror displays that replace side-view mirrors of automobiles, and displays arranged on the backside of front seats as entertainment for back seats of automobiles.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, embodiments of the invention will be described in detail with reference to the accompanying drawings.

Figure 1B:
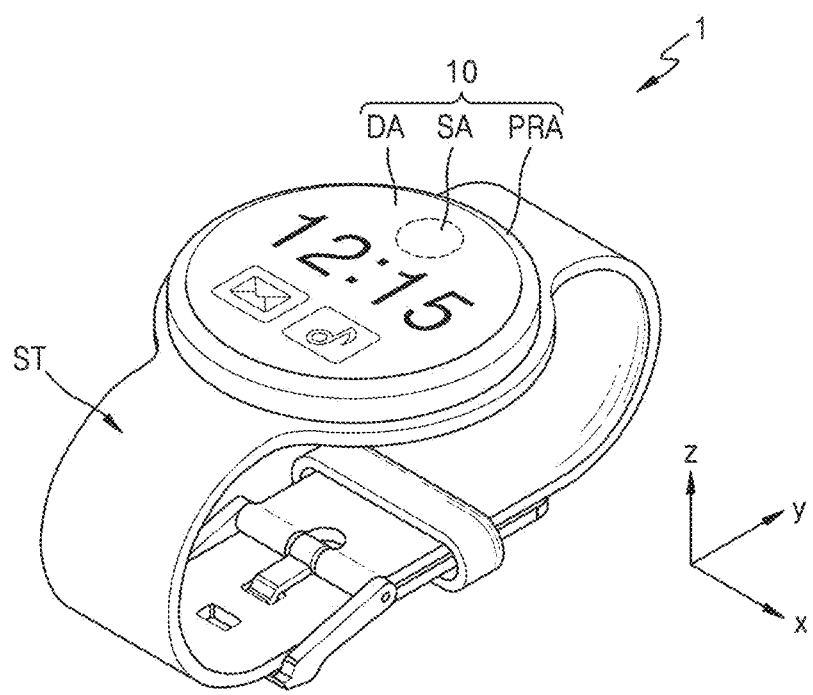
Figure 1C:
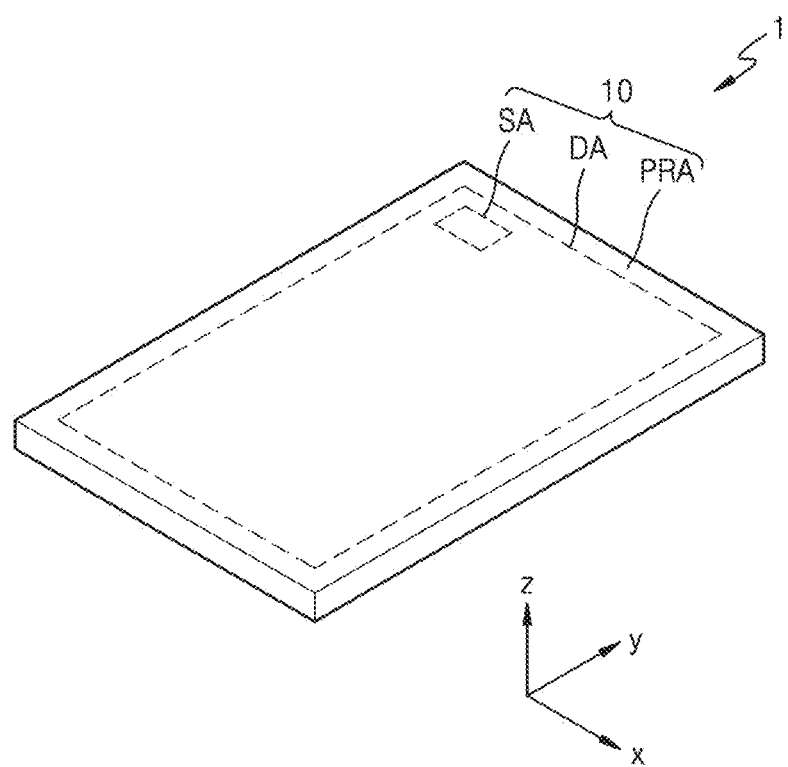

FIGS. 1A to 1C are views schematically illustrating a display device 1 according to various embodiments.

An embodiment of the display device 1 may be configured to display an image. In an embodiment, the display device 1 may display a diagnosis result of various illnesses. In one embodiment, for example, the display device 1 may sense a target material in a gaseous or liquid state emitted or discharged from a user, and display a diagnosis result of an illness, from which the user is suffering, from the sensed target material. The target material may include a material included in gas such as breath, vaporized sweat, or the like, or may include a material included in liquid such as sweat, saliva, tears, or the like. In an alternative embodiment, the display device 1 may display a diagnosis result of a body condition of the user. In one embodiment, for example, the display device 1 may sense a target material in a gaseous or liquid state emitted or discharged from the user, and display a diagnosis result of the body condition of the user from the sensed target material.

In an embodiment, the display device 1 may include a display panel 10. The display panel 10 may include a plurality of pixels (not shown) and may be configured to display an image. The display panel 10 may include a display area DA, a sensor area SA, and a peripheral area PRA. In such an embodiment, the display area DA may be defined on a plane defined by an x direction and a y direction. Here, z direction may be a direction perpendicular to the x direction and the y direction, or a thickness direction of the display device 1.

The display area DA may include a plurality of pixels arranged therein. Thus, the display panel 10 may be configured to display an image in the display area DA using light emitted by the plurality of pixels.

The sensor area SA may include an area for detecting a target material in a gaseous or liquid state. In an embodiment, a discoloration sensor layer that is discolored when exposed to the target material may be arranged in the sensor area SA. In an embodiment, it may be identified whether the target material is present by irradiating light on the discoloration sensor layer and identifying the reflected light. In an alternative embodiment, a sensor circuit layer including a sensor thin-film transistor that varies in resistance when exposed to a target material may be arranged in the sensor area SA. In such an embodiment, it may be identified whether the target material is present by measuring a current or resistance value flowing in the sensor circuit layer.

In an embodiment, the sensor area SA may have a polygonal shape. In an alternative embodiment, the sensor area SA may be circular or elliptical. In another alternative embodiment, the sensor area SA may have round edges.

In an embodiment, the display area DA may at least partially surround the sensor area SA. In one embodiment, for example, the display area DA may entirely surround the sensor area SA. In an alternative embodiment, the display area DA may surround only a portion of the sensor area SA.

The peripheral area PRA may include an area in which no image is provided. The peripheral area PRA may at least partially surround the display area DA and the sensor area SA. In an embodiment, the peripheral area PRA may entirely surround the display area DA and the sensor area SA. A driver or the like for providing electric signals or power to the pixels may be arranged in the peripheral area PRA. In an embodiment, a controller (not shown) for determining whether the target material is present may be arranged in the peripheral area PRA. The controller may control the display panel 10 to display information on whether the target material is present. Thus, the display device 1 may display the information on whether the target material is present.

Referring to FIG. 1A, an embodiment of the display device 1 may be attached to a user. In an embodiment, the display device 1 may include an adhesive layer and may be attached to the user. In such an embodiment, the display device 1 may be deformed in various shapes. In one embodiment, for example, the display device 1 may be deformed according to a shape of the skin surface of the user.

Referring to FIG. 1B, an alternative embodiment of the display device 1 may be used in wearable devices such as smart watches. In an embodiment, the display device 1 may be coupled to a watch strap ST.

Referring to FIG. 1C, another alternative embodiment of the display device 1 may be used as a screen of portable electronic devices such as mobile phones. Hereinafter, for convenience of description, embodiments where the display device 1 is attached to the user as shown in FIG. 1A will be described in detail.

FIG. 2 is a cross-sectional view schematically illustrating a display device 1 according to an embodiment. FIG. 2 is a cross-sectional view illustrating the display device 1 in FIG. 1A, taken along line A-A'.

Referring to FIG. 2, an embodiment of the display device 1 may include the display panel 10, a discoloration sensor layer 20, a light detection layer 30, a lower cover 40, an upper cover 50, and an adhesive layer 60.

In an embodiment, the display panel 10 may include an upper surface 10US and a lower surface 10LS. In an embodiment, the lower surface 10LS of the display panel 10 may be a surface opposite to the upper surface 10US of the display panel 10. In an embodiment, the lower cover 40 may be disposed on the lower surface 10LS of the display panel 10. The upper cover 50 may be disposed on the upper surface 10US of the display panel 10.

The display panel 10 may include the sensor area SA and the display area DA. The sensor area SA may include an area exposed to a target material. The display panel 10 may be configured to display images in the display area DA. In an embodiment, a display element DPE may be arranged in the sensor area SA and the display area DA. In an alternative embodiment, the display element DPE may be arranged only in the display area DA among the sensor area SA and the display area DA.

The display panel 10 may include a through portion TP. The through portion TP may be defined through the display panel 10 from the upper surface 10US to the lower surface 10LS. The through portion TP may not have elements of the display panel 10 arranged therein. The display panel 10 includes the through portion TP, and thus may be freely stretched and/or contracted. When a tensile force or a contractile force is exerted on the display panel 10 including the through portion TP, relatively low stress may be exerted on the display panel 10. Thus, the through portion TP may effectively prevent or substantially reduce damage to the display panel 10.

The through portion TP may include a first through portion TP1 and a second through portion TP2. The first through portion TP1 may overlap the sensor area SA. The first through portion TP1 may overlap the discoloration sensor layer 20. Thus, at least a portion of the discoloration sensor layer 20 may be exposed by the first through portion TP1. In an embodiment, the first through portion TP1 may be provided plural in the sensor area SA. The second through portion TP2 may overlap the display area DA. In an embodiment, the second through portion TP2 may be provided plural in the display area DA. In an alternative embodiment, the second through portion TP2 may be omitted.

The display panel 10 may include a substrate 100, a display layer 200, and an encapsulation layer 300. The substrate 100 may include glass or a polymer resin, such as polyethersulfone, polyarylate, polyetherimide, polyethylene naphthalate, polyethylene terephthalate, polyphenylene sulfide, polyimide, polycarbonate, cellulose triacetate, or cellulose acetate propionate. The substrate 100 including the polymer resin may be flexible, rollable, or bendable. The substrate 100 may have a multi-layer structure including a base layer including at least one selected from the above-listed polymer resins, and a barrier layer.

The display layer 200 may be disposed on the substrate 100. The display layer 200 may include the display element DPE. The display element DPE may include an organic light-emitting diode including an organic emission layer. In an embodiment, the display element DPE may include a light-emitting diode ("LED"). A size of the LED may be a micro scale or a nano scale. In one embodiment, for example, the LED may include a micro LED. In an embodiment, the LED may include a nanorod LED. The nanorod LED may include gallium nitride (GaN). In an embodiment, a color conversion layer may be disposed on the nanorod LED. The color conversion layer may include quantum dots. In an embodiment, the display element DPE may include a quantum dot LED including a quantum dot emission layer. In an alternative embodiment, the display element DPE may include an inorganic LED including an inorganic semiconductor. In an embodiment, the display layer 200 may include a pixel circuit layer 210 and a display element layer 220.

In an embodiment, the pixel circuit layer 210 may be disposed on the substrate 100. The pixel circuit layer 210 may include a pixel circuit for controlling the display element DPE. In an embodiment, the pixel circuit may include at least one thin-film transistor. The pixel circuit layer 210 may further include an insulating layer including an inorganic material and/or an organic material.

In an embodiment, the display element layer 220 may be disposed on the pixel circuit layer 210. The display element layer 220 may include the display element DPE. The display element DPE may be electrically connected to the pixel circuit. In an embodiment, the display element DPE may emit light to the upper surface 10US of the display panel 10. In an alternative embodiment, the display element DPE may emit light to the lower surface 10LS of the display panel 10. In another alternative embodiment, the display element DPE may emit light to the upper surface 10US of the display panel 10 and the lower surface 10LS of the display panel 10.

The display element DPE may be provided plural. In an embodiment, a plurality of display elements DPE may include a first display element DPE1 and a second display element DPE2. The first display element DPE1 may be arranged in the sensor area SA. The first display element DPE1 may be provided plural in the sensor area SA. In an embodiment, the first display element DPE1 may emit light to the discoloration sensor layer 20. In such an embodiment, the first display element DPE1 may include a light source that irradiates light on the discoloration sensor layer 20. The second display element DPE2 may be arranged in the display area DA. The second display element DPE2 may be provided plural in the display area DA. A plurality of second display elements DPE2 may emit light and display an image.

The encapsulation layer 300 may be disposed on the display layer 200. The encapsulation layer 300 may cover the display element DPE. In an embodiment, the encapsulation layer 300 may include at least one inorganic encapsulation layer and at least one organic encapsulation layer. The at least one inorganic encapsulation layer may include at least one inorganic material selected from among aluminum oxide ($Al_2O_3$), titanium oxide ($TiO_2$), tantalum oxide ($Ta_2O_5$), zinc oxide (ZnO), silicon oxide ($SiO_2$), silicon nitride ($SiN_x$), and silicon oxynitride (SiON). The at least one organic encapsulation layer may include a polymer-based material. The polymer-based material may include an acryl-based resin, an epoxy-based resin, polyimide, polyethylene, or the like. In an embodiment, the at least one organic encapsulation layer may include acrylate.

In an alternative embodiment, the encapsulation layer 300 may have a structure in which an inner space between the substrate 100 and an upper substrate, which is a transparent substrate, is sealed by coupling the substrate 100 and the upper substrate to each other using an encapsulation member. In such an embodiment, a moisture absorbent, a filler, or the like may be arranged in the inner space. A sealing member may be sealant, and in an alternative embodiment, may include a material cured by laser. In one embodiment, for example, the sealing member may include frit. In one embodiment, for example, the sealing member may include a urethane-based resin, an epoxy-based resin, and an acryl-based resin as organic sealants, and silicon or the like as an inorganic sealant. In one embodiment, for example, the urethane-based resin may include urethane acrylate or the like. The acryl-based resin may include, for example, butyl acrylate, ethylhexyl acrylate, or the like. In an embodiment, the sealing member may include a material cured by heat. In an alternative embodiment, the encapsulation layer 300 may be omitted.

Although not shown, a touch electrode layer may be disposed on the encapsulation layer 300, and an optical functional layer may be disposed on the touch electrode layer. The touch electrode layer may obtain coordinate information corresponding to an external input, for example, a touch event. The optical functional layer may reduce the reflectivity of (external) light incident toward the display device from the outside, and/or improve color purity of light emitted from the display device. In an embodiment, the optical functional layer may include a retarder and/or a polarizer. The retarder may include a film-type retarder or a liquid crystal coating-type retarder, and may include a λ/2 retarder and/or a λ/4 retarder. The polarizer may also include a film-type polarizer or a liquid crystal coating-type polarizer. The film-type polarizer may include a stretchable synthetic resin film, and the liquid crystal coating-type polarizer may include liquid crystals arranged in a certain array. The retarder and the polarizer may further include a protective film.

In an alternative embodiment, the optical functional layer may include a black matrix and color filters. The color filters may be arranged considering a color of light emitted by pixels of the display panel. Each of the color filters may include a red, green, or blue pigment or dye. In some embodiments, each of the color filters may further include quantum dots in addition to the above-described pigment or dye. In an embodiment, some of the color filters may not include the above-described pigment or dye, but may include scattering particles including $TiO_2$.

In another alternative embodiment, the optical functional layer may include a destructive interference structure. The destructive interference structure may include a first reflective layer and a second reflective layer on different layers from each other. First reflected light and second reflected light respectively reflected from the first reflective layer and the second reflective layer may destructively interfere with each other, thereby reducing the reflectivity of external light.

An adhesive member may be arranged between the touch electrode layer and the optical functional layer. As the adhesive member, a common member known in the art may be employed without limitation. In one embodiment, for example, the adhesive member may include a pressure sensitive adhesive ("PSA").

The discoloration sensor layer 20 may be discolored when exposed to a target material. In an embodiment, when exposed to the target material, the discoloration sensor layer 20 may be discolored from a first color to a second color. In one embodiment, for example, the first display element DPE1 may irradiate light having a reference wavelength band on the discoloration sensor layer 20. The discoloration sensor layer 20 may reflect light having a first wavelength band. In such an embodiment, the discoloration sensor layer 20 may reflect the light having the first wavelength band from among the light having the reference wavelength band, and absorb light of the remaining wavelength bands other than the first wavelength band. When the discoloration sensor layer 20 is exposed to the target material, the discoloration sensor layer 20 may reflect light having a second wavelength band. In such an embodiment, the discoloration sensor layer 20 may reflect the light having the second wavelength band from among the light having the reference wavelength band, and absorb light of the remaining wavelength bands other than the second wavelength band. In such an embodiment, the first wavelength band and the second wavelength band may be different from each other. In an embodiment, the discoloration sensor layer 20 may include an M13 bacteriophage. In such an embodiment, the M13 bacteriophage may overlap the sensor area SA. When the M13 bacteriophage is exposed to the target material, the arrangement of bundles of M13 bacteriophage may be changed.

The discoloration sensor layer 20 may be arranged in the sensor area SA. In an embodiment, the discoloration sensor layer 20 may be disposed on any of the upper surface 10US of the display panel 10 and the lower surface 10LS of the display panel 10. In one embodiment, for example, the discoloration sensor layer 20 may be disposed on the upper surface 10US of the display panel 10.

The discoloration sensor layer 20 may overlap the first through portion TP1. In an embodiment, the discoloration sensor layer 20 may overlap a plurality of first through portions TP1. The discoloration sensor layer 20 may be exposed by the first through portion TP1. Thus, the target material may reach the discoloration sensor layer 20 through the first through portion TP1.

The light detection layer 30 may detect light. In an embodiment, the light detection layer 30 may detect discoloration of the discoloration sensor layer 20. Light reflected from the discoloration sensor layer 20 may be incident on the light detection layer 30. In one embodiment, for example, light having the first wavelength band may be incident on the light detection layer 30. In such an embodiment, the light detection layer 30 may detect the light having the first wavelength band. Light having the second wavelength band may be incident on the light detection layer 30. In such an embodiment, the light detection layer 30 may detect the light having the second wavelength band. Thus, the light detection layer 30 may detect discoloration of the discoloration sensor layer 20.

The light detection layer 30 may be arranged in the sensor area SA. In an embodiment, the light detection layer 30 may be disposed on the discoloration sensor layer 20. In an embodiment, the light detection layer 30 may face the upper surface 10US of the display panel 10. The discoloration sensor layer 20 may be arranged between the light detection layer 30 and the display panel 10.

In an embodiment, the light detection layer 30 may include a photodiode and a color filter. In such an embodiment, the color filter may be arranged between the photodiode and the discoloration sensor layer 20.

The lower cover 40 may be arranged under the display panel 10. In an embodiment, the lower cover 40 may face the lower surface 10LS of the display panel 10. The lower cover 40 may be disposed on the lower surface 10LS of the display panel 10. The lower cover 40 may overlap the second through portion TP2. In an embodiment, the lower cover 40 may block the second through portion TP2.

The lower cover 40 may include a lower hole 40H overlapping the first through portion TP1. The lower hole 40H may be defined through the lower cover 40 from an upper surface of the lower cover 40 to a lower surface of the lower cover 40. The upper surface of the lower cover 40 may be a surface facing the lower surface 10LS of the display panel 10. The lower surface of the lower cover 40 may be a surface opposite to the upper surface of the lower cover 40. The lower hole 40H may overlap the sensor area SA. In an embodiment, the lower hole 40H may be provided plural. In an embodiment, as show in FIG. 2, one lower hole 40H may be defined to overlap one first through portion TP1, but not being limited thereto. In an alternative embodiment, one lower hole 40H may be defined to overlap a plurality of first through portions TP1. In an embodiment, a size of the lower hole 40H may be greater than or equal to a size of the first through portion TP1. The size of the lower hole 40H may be defined by an area of the lower hole 40H. The size of the first through portion TP1 may be defined by an area of the first through portion TP1. The target material may reach the discoloration sensor layer 20 through the lower hole 40H and the first through portion TP1.

The lower cover 40 may include an elastomer. In one embodiment, for example, the elastomer may include a polymer material exhibiting rubber elasticity. In an embodiment, the lower cover 40 may include a synthetic resin. In one embodiment, for example, the synthetic resin may include polyolefin, polyvinyl chloride, elastomeric silicone, elastomeric polyurethane, elastomeric polyisoprene, or the like. Thus, the lower cover 40 may be stretched and/or contracted. In such an embodiment, even when the lower cover 40 overlaps the second through portion TP2, the display panel 10 may not be damaged by stretching and/or contraction.

The upper cover 50 may face the upper surface 10US of the display panel 10. The upper cover 50 may cover the display panel 10, the discoloration sensor layer 20, and the light detection layer 30. The upper cover 50 may include an elastomer. In an embodiment, the upper cover 50 may include a synthetic resin. In one embodiment, for example, the synthetic resin may include polyolefin, polyvinyl chloride, elastomeric silicone, elastomeric polyurethane, elastomeric polyisoprene, or the like.

The adhesive layer 60 may allow the display device 1 to be attached to a user. The adhesive layer 60 may be arranged under the lower cover 40. In an embodiment, the adhesive layer 60 may face a lower surface of the lower cover 40. In one embodiment, for example, an upper surface of the adhesive layer 60 may face the lower surface of the lower cover 40. The lower surface of the adhesive layer 60 may be a surface opposite to the upper surface of the adhesive layer 60. The lower surface of the adhesive layer 60 may be a surface attached to the user.

In an embodiment, the adhesive layer 60 may have an adhesive layer hole 60H overlapping the sensor area SA. The adhesive layer hole 60H may penetrate through the upper surface of the adhesive layer 60 and the lower surface of the adhesive layer 60. Thus, a target material may reach the discoloration sensor layer 20 through the adhesive layer hole 60H, the lower hole 40H, and the first through portion TP1. In an embodiment, as show in FIG. 2, a single adhesive layer hole 60H may be defined to overlap the sensor area SA, but not being limited thereto. In an alternative embodiment, a plurality of adhesive layer holes 60H may be defined through the adhesive layer 60, and the plurality of adhesive layer holes 60H may overlap the sensor area SA. The adhesive layer 60 may include a common adhesive material known in the art. In an alternative embodiment, the adhesive layer 60 may be omitted.

In an embodiment, the display device 1 may include a controller (not shown). The controller may be electrically connected to the light detection layer 30. Thus, the controller may determine whether the target material is present considering information obtained through the light detection layer 30.

In an embodiment of the display device 1 according to invention, the through portion TP is defined through the display panel 10, and thus, a shape of the display device 1 may be changed relatively freely. Thus, the display device 1 may be deformed in a shape corresponding to a shape of a user's skin and attached to the user's skin.

In an embodiment of the display device 1 according to the invention, the target material may reach the discoloration sensor layer 20 via the first through portion TP1 of the display panel 10. When the target material reaches the discoloration sensor layer 20, the discoloration sensor layer 20 may be discolored. In an embodiment, the target material may be in a gaseous state. In one embodiment, for example, the target material may be a material generated by vaporizing a user's sweat. In an embodiment, the first display element DPE1 is arranged in the sensor area SA of the display panel 10, and thus, light may be irradiated to the discoloration sensor layer 20, and the light detection layer 30 may detect a color change of the discoloration sensor layer 20. The light detection layer 30 may obtain information on the color change, and the controller may determine whether the target material is present based on the information. In such an embodiment, the controller may control the display panel 10 to display a diagnosis result in the display area DA. As described above, in an embodiment of the display device 1, a system for detecting a target material may be simplified.

In an embodiment, the display panel 10 of the display device 1 may include the first display element DPE1 and the second display element DPE2. The first display element DPE1 arranged in the sensor area SA may include a light source of the discoloration sensor layer 20, and a second display element DPE2 arranged in the display area DA may emit light to display an image. Thus, a target material may be sensed and displayed using a single display panel 10.

Figure 3:
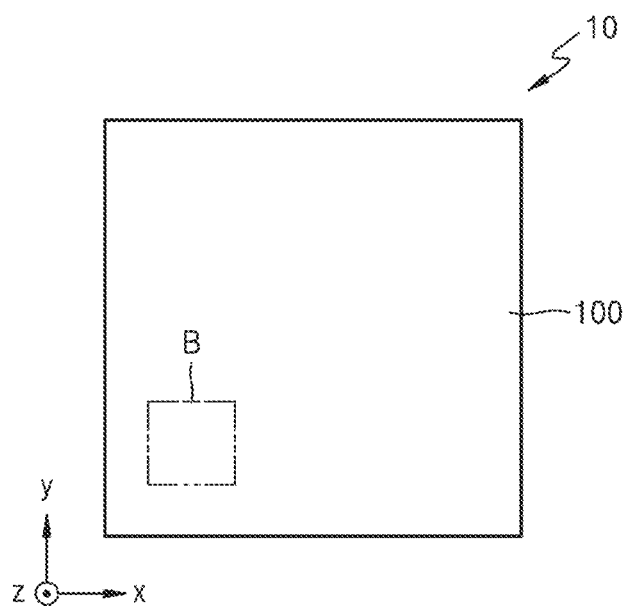
FIG. 3 is a plan view schematically illustrating a display panel according to an embodiment.

FIG. 3 is a plan view schematically illustrating a display panel 10 according to an embodiment.

Referring to FIG. 3, an embodiment of the display panel 10 may include a substrate 100 and a multi-layer disposed on the substrate 100. In an embodiment, the display panel 10 may include a through portion (not shown). The substrate 100 and the multi-layer may not be arranged in the through portion. In such an embodiment, the through portion may be an empty space in the display panel 10. The through portion may be provided plural in the display panel 10. In such an embodiment, where the display panel 10 includes a plurality of through portions, the flexibility of the display panel 10 may be improved.

Figure 4:
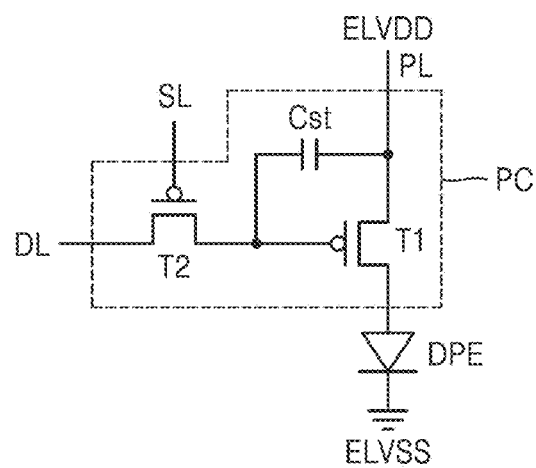
FIG. 4 is an equivalent circuit diagram schematically illustrating an embodiment of a pixel circuit in a display panel.

FIG. 4 is an equivalent circuit diagram schematically illustrating an embodiment of a pixel circuit PC in a display panel.

Referring to FIG. 4, an embodiment of the pixel circuit PC may be connected to a display element DPE. The pixel circuit PC may include a driving thin-film transistor T1, a switching thin-film transistor T2, and a storage capacitor Cst. In such an embodiment, the display element DPE may emit one of red, green, and blue light, or may emit one of red, green, blue, and white light.

The switching thin-film transistor T2 is connected to a scan line SL and a data line DL, and may transfer, to the driving thin-film transistor T1, a data signal or a data voltage received via the data line DL in response to a scan signal or a switching voltage received via the scan line SL.

The storage capacitor Cst is connected to the switching thin-film transistor T2 and a driving voltage line PL, and may store a voltage corresponding to a voltage difference between the voltage received from the switching thin-film transistor T2 and a first power voltage ELVDD applied to the driving voltage line PL.

The driving thin-film transistor T1 is connected to the driving voltage line PL and the storage capacitor Cst, and may control a driving current flowing in the display element DPE from the driving voltage line PL based on the voltage value stored in the storage capacitor Cst. The display element DPE may emit light having a luminance according to the driving current. An opposite electrode of the display element DPE may receive a second power voltage ELVSS.

In an embodiment, as show in FIG. 4, the pixel circuit PC includes two thin-film transistors and a single storage capacitor, but not being limited thereto. Alternatively, the pixel circuit PC may include three or more thin-film transistors.

Figure 5A:
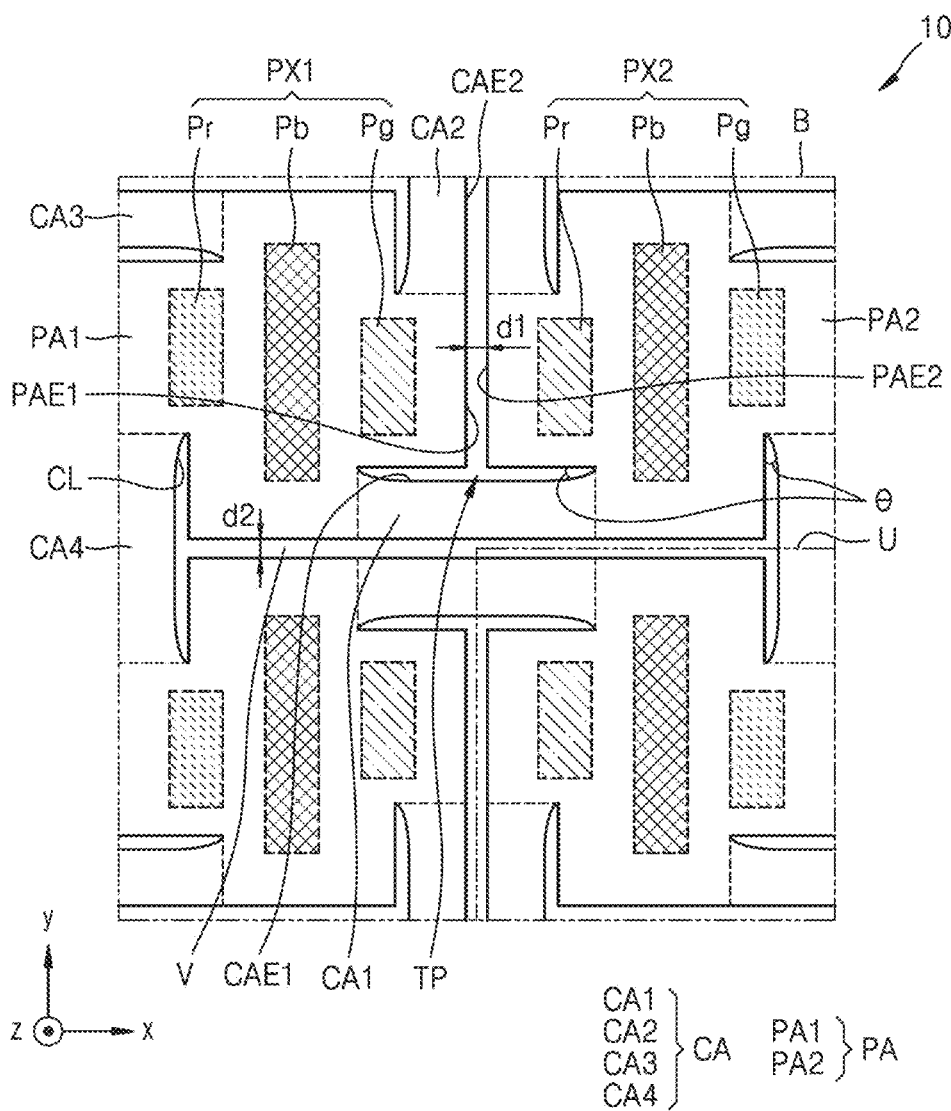
FIG. 5A is an enlarged view of a portion of the display panel of FIG. 3.
Figure 5B:
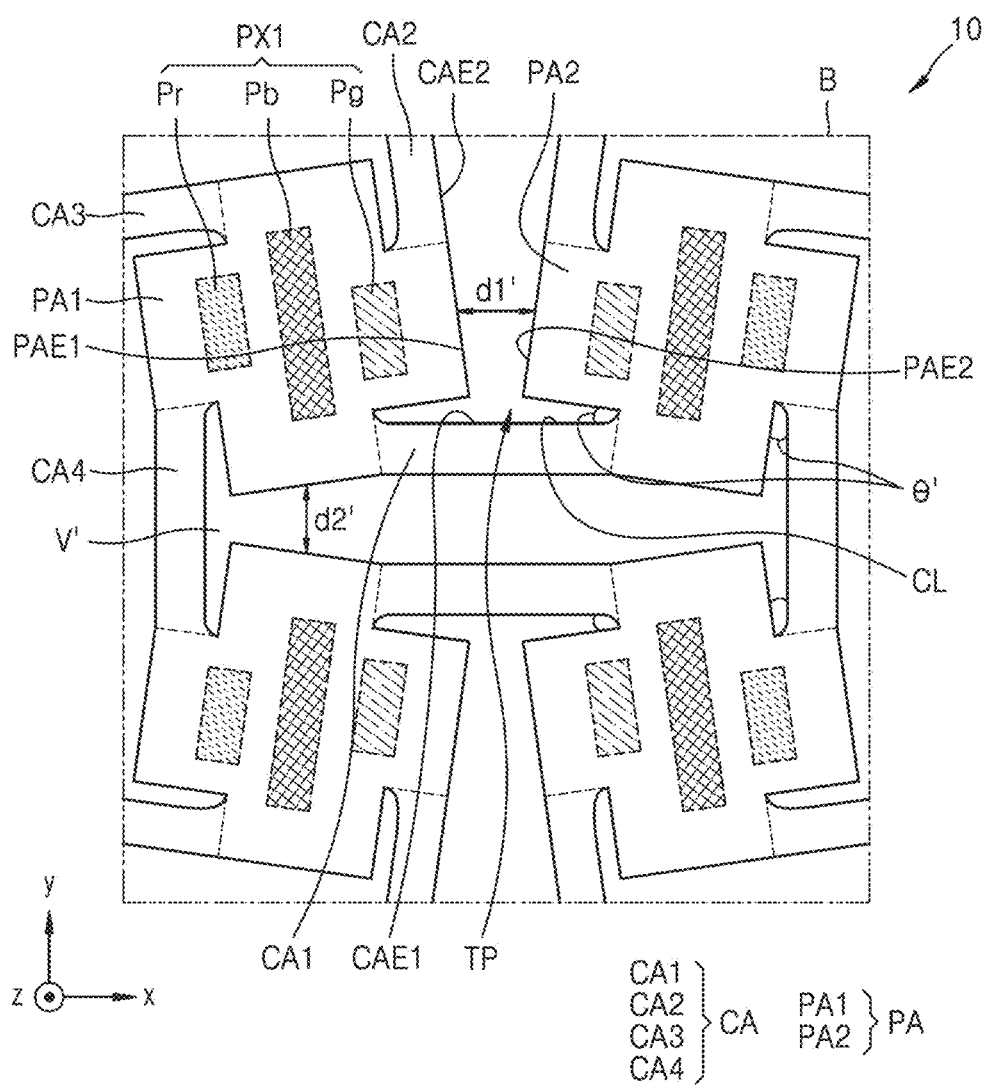
FIG. 5B is a plan view illustrating that the display panel of FIG. 5A is in a stretched state in a first direction and a second direction.

FIG. 5A is an enlarged view of a region B of the display panel 10 in FIG. 3. FIG. 5B is a plan view illustrating a state in which the display panel in FIG. 5A is stretched in a first direction and a second direction.

Referring to FIG. 5A, an embodiment of the display panel 10 may include a pixel area PA and a connection area CA. The pixel area PA may include a first pixel area PA1 and a second pixel area PA2. In an embodiment, the display panel 10 may include a plurality of first pixel areas PA1 and a plurality of second pixel areas PA2. The display panel 10 may include a plurality of connection areas CA. In one embodiment, for example, the connection area CA may include a first connection area CA1, a second connection area CA2, a third connection area CA3, and a fourth connection area CA4.

The plurality of pixel areas PA may be apart from each other in a first direction and/or a second direction. In an embodiment, the first direction and the second direction may be perpendicular to each other. In one embodiment, for example, the first direction may be an x direction or a −x direction of FIGS. 5A and 5B, and the second direction may be a y direction or a −y direction of FIGS. 5A and 5B. In an alternative embodiment, the first direction and the second direction may form an acute angle or an obtuse angle. Hereinafter, embodiments where the first direction (for example, the x direction or the −x direction) and the second direction (for example, the y direction or the −y direction) are perpendicular to each other will be mainly described in detail.

The first pixel area PA1 and the second pixel area PA2 may be apart from each other in the first direction (for example, the x direction or the −x direction) and the second direction (for example, the y direction or the −y direction). In an embodiment, a plurality of pixel areas PA adjacent to each other may be apart from one another in the first direction (for example, the x direction or the −x direction) by a first distance d1. In an embodiment, the plurality of pixel areas PA adjacent to each other may be apart from each another in the second direction (for example, the y direction or the −y direction) by a second distance d2.

The first pixel area PA1 may be connected to at least one connection area CA. In one embodiment, for example, the first pixel area PA1 may be connected to one connection area CA. In one alternative embodiment, for example, the first pixel area PA1 may be connected to a plurality of connection areas CA.

The second pixel area PA2 may be connected to at least one connection area CA. In one embodiment, for example, the second pixel area PA2 may be connected to one connection area CA. In one alternative embodiment, for example, the second pixel area PA2 may be connected to a plurality of connection areas CA. The second pixel area PA2 may be similar to the first pixel area PA1.

The connection area CA may extend between pixel areas PA that are adjacent to each other. In an embodiment, each of the pixel areas PA may be connected to four connection areas CA. Four connection areas CA connected to one pixel area PA may extend in different directions from each other, and may be connected to another pixel area PA adjacent to the one pixel area PA described above.

In an embodiment, the connection area CA may extend to the second pixel area PA2 from the first pixel area PA1. The first pixel area PA1 and the second pixel area PA2 may be connected to each other by the connection area CA. In one embodiment, for example, the first connection area CA1 may extend to the second pixel area PA2 from the first pixel area PA1. In an embodiment, the first pixel area PA1 and the second pixel area PA2 may be connected to the first connection area CA1, and the first pixel area PA1, the second pixel area PA2 and the first connection area CA1 may be integrally provided as a single unitary body.

One of the plurality of connection areas CA may extend in the first direction (for example, the x direction or the −x direction). Another of the plurality of connection areas CA may extend in the second direction (for example, the y direction or the −y direction) crossing the first direction. In one embodiment, for example, the first connection area CA1 and the third connection area CA3 may extend in the first direction (for example, the x direction or the −x direction). The second connection area CA2 and the fourth connection area CA4 may extend in the second direction (for example, the y direction or the −y direction).

A through portion TP may be defined in the display panel 10. The through portion TP may penetrate through the display panel 10. The through portion TP may extend from an upper surface of the display panel 10 to a lower surface of the display panel 10. Thus, elements of the display panel 10 may not be arranged in the through portion TP. The display panel 10 with the through portion TP may have improved flexibility.

In an embodiment, at least a portion of the through portion TP may be defined by an edge PAE1 of the first pixel area PA1, an edge PAE2 of the second pixel area PA2, and an edge CAE1 of the first connection area CA1. In an embodiment, at least a portion of the through portion TP may be defined by the edge PAE1 of the first pixel area PA1, the edge PAE2 of the second pixel area PA2, the edge CAE1 of the first connection area CA1, and an edge CAE2 of the second connection area CA2.

One pixel area PA and a portion of the connection areas CA extending therefrom may be defined as one basic unit U. The basic unit U may be repeatedly arranged in the first direction (for example, the x direction or the −x direction) and the second direction (for example, the y direction or the −y direction), and it may be understood that the display panel 10 is provided by interconnecting the basic units U, which are repeatedly arranged, to each other. Two basic units U adjacent to each other may be symmetrical to each other. In one embodiment, for example, in FIG. 5A, two basic units U adjacent to each other in a left and right direction may be horizontally symmetrical to each other with respect to a symmetry axis located between the two basic units U and parallel to the second direction (for example, the y direction or the −y direction). In such an embodiment, two basic units U vertically adjacent to each other in an up and down direction may be vertically symmetrical to each other with respect to a symmetry axis located between the two basic units U and parallel to the first direction (for example, the x direction or the −x direction).

Basic units U adjacent to each other among the plurality of basic units U, for example, the four basic units U shown in FIG. 5A, form a closed loop CL therebetween, and the closed loop CL may define a space area V that is an empty space. The space area V may be defined by the closed loop CL provided by the edges of the plurality of pixel areas PA and the edges of the plurality of connection areas CA. The space area V may overlap or define the through portion TP of the display panel 10.

In an embodiment, an angle θ between the edge CAE1 of the connection area CA and the edge PAE2 of the second pixel area PA2 may be an acute angle. When an external force for pulling the display panel 10 is exerted, as shown in FIG. 5B, an angle θ' (θ'>θ) between the edge CAE1 of the first connection area CA1 and the edge PAE2 of the second pixel area PA2 may increase, an area or shape of a space area V' may be changed, and a location of the pixel area PA may also be changed.

When the above-described external force is exerted, according to the change in angle θ', the increase in area of the space area V', and/or the deformation of the space area V', each of the pixel areas PA may be rotated at a certain angle. As each of the pixel areas PA rotates, a distance between the pixel areas PA, for example, a first distance d1' and a second distance d2', may vary for each location.

When an external force for pulling the display panel 10 is exerted, stress may concentrate on the edge CAE1 of the first connection area CA1 and the edge PAE2 of the second pixel area PA2. In this case, the closed loop CL defining the space area V may include a curved line to prevent damage to the display panel 10.

A first pixel PX1 and a second pixel PX2 may be arranged in the first pixel area PA1 and the second pixel area PA2, respectively. In an embodiment, each of the first pixel PX1 and the second pixel PX2 may include a red sub-pixel Pr, a green sub-pixel Pg, and a blue sub-pixel Pb. The red sub-pixel Pr, the green sub-pixel Pg, and the blue sub-pixel Pb may emit red, green, and blue light, respectively. In an alternative embodiment, each of the first pixel PX1 and the second pixel PX2 may include the red sub-pixel Pr, the green sub-pixel Pg, the blue sub-pixel Pb, and a white sub-pixel. The red sub-pixel Pr, the green sub-pixel Pg, the blue sub-pixel Pb, and the white sub-pixel may emit red, green, blue, and white light, respectively. Hereinafter, embodiments where each of the first pixel PX1 and the second pixel PX2 includes the red sub-pixel Pr, the green sub-pixel Pg, and the blue sub-pixel Pb will be mainly described in detail.

Each of a sub-pixel arrangement structure of the first pixel PX1 and a sub-pixel arrangement structure of the second pixel PX2 may be provided in a stripe structure. In one embodiment, for example, the red sub-pixel Pr, the green sub-pixel Pg, and the blue sub-pixel Pb may be arranged side by side in the first direction (for example, the x direction or the −x direction) or the second direction (for example, the y direction or the −y direction). In an alternative embodiment, each of the sub-pixel arrangement structure of the first pixel PX1 and the sub-pixel arrangement structure of the second pixel PX2 may be an S-stripe structure. In another alternative embodiment, each of the sub-pixel arrangement structure of the first pixel PX1 and the sub-pixel arrangement structure of the second pixel PX2 may be a pentile structure.

In an embodiment, the display panel 10 as described above may be applied to the sensor area SA in FIG. 2. In an embodiment, the display panel 10 as described above may be applied to the sensor area SA and the display area DA in FIG. 2.

Figure 6A:
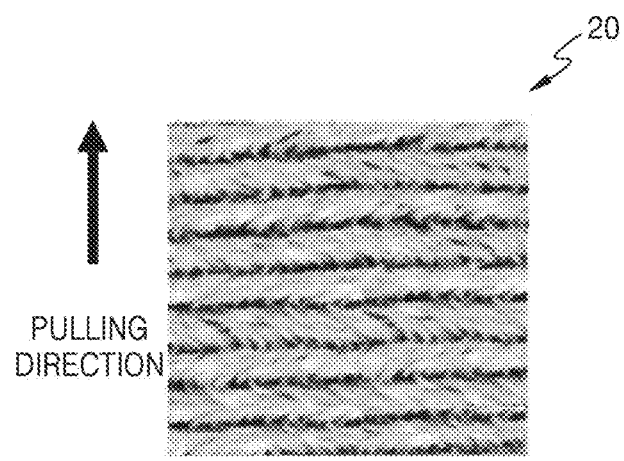
FIGS. 6A to 6E are images illustrating a M13 bacteriophage of a discoloration sensor layer according to an embodiment.
Figure 6B:
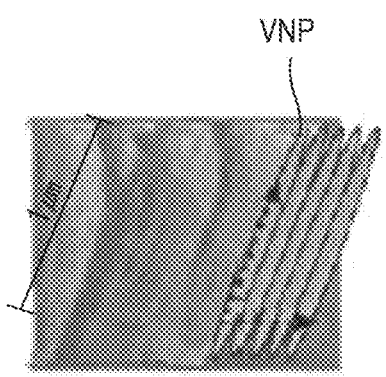
Figure 6C:
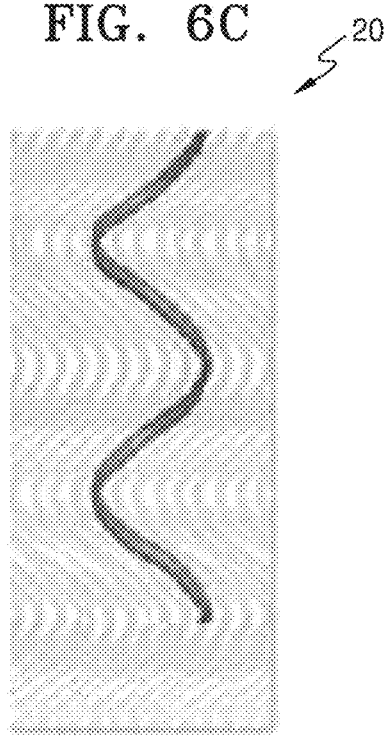
Figure 6D:
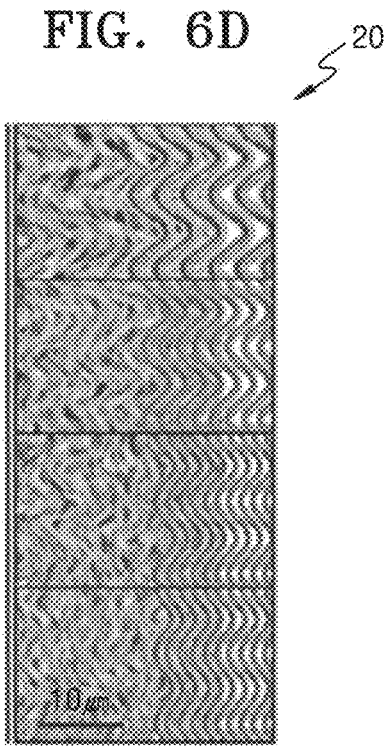
Figure 6E:
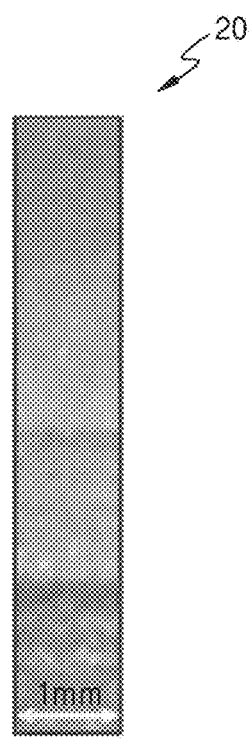

FIGS. 6A to 6E are images of an M13 bacteriophage VNP of the discoloration sensor layer 20 according to an embodiment. FIG. 6A is an image in which the M13 bacteriophages of the discoloration sensor layer 20 include a smectic spiral nanofiber structure. FIG. 6B is an enlarged image of the M13 bacteriophage VNP in FIG. 6A in a size of 1 micrometer (μm). FIG. 6C is an image of any of smectic spiral nanofiber bundles of the discoloration sensor layer 20. FIG. 6D is an image of M13 bacteriophage arrangements in a size of 10 μm that are different for each area of the discoloration sensor layer 20. FIG. 6E shows the discoloration sensor layer 20 in a size of 1 mm and light reflected by an M13 bacteriophage in an arrangement of FIG. 6D.

Referring to FIGS. 6A to 6C, in an embodiment, the discoloration sensor layer 20 may include an M13 bacteriophage VNP. The M13 bacteriophage VNP may include a tube-shaped nanoparticle having a length of about 880 millimeters (mm) and a diameter of about 6.6 nanometers (nm). The M13 bacteriophage VNP includes a protein particle manifested through a constant gene, and thus may be substantially constant in size, shape, and distribution. In such an embodiment, almost all the M13 bacteriophages VNP may have a substantially same size and shape as each other. The M13 bacteriophage VNP may include about 2,700 pairs of protein VIII (hereinafter referred to as pVIII) for each and four or five pairs of protein (pill, pVI, pVII, and pIX) at both ends thereof.

In an embodiment of the M13 bacteriophage VNP protein including an amino acid sequence may be provided in pVIII, which is a main surface protein of the M13 bacteriophage.

In the discoloration sensor layer 20, a plurality of M13 bacteriophages VNP may be provided in a smectic spiral nanofiber structure. In one embodiment, for example, a smectic spiral nanofiber structure may be provided in which the plurality of M13 bacteriophages VNP are arranged in a smectic structure and bundles including the M13 bacteriophages VNP are pulled in a spiral shape.

Referring to FIGS. 6D and 6E, the discoloration sensor layer 20 may exhibit different colors from each other for each area. In an embodiment, because the thicknesses of the bundles of smectic spiral nanofibers are different from each other in a plurality of areas, the discoloration sensor layer 20 may include areas exhibiting different colors from each other. The thickness of the bundle of smectic spiral nanofibers may be determined by adjusting a pulling speed, a concentration of a prepared solution, or the like, in a manufacturing process of the discoloration sensor layer 20.

When the discoloration sensor layer 20 is exposed to a target material, an arrangement of bundles of M13 bacteriophage VNP included in the discoloration sensor layer 20 may be changed. Thus, a length of a wavelength reflecting light incident on the discoloration sensor layer 20 may be changed, such that a visible color is changed, and discoloration is performed. Thus, it may be detected whether the target material is present through the color change of the discoloration sensor layer 20.

Figure 7:
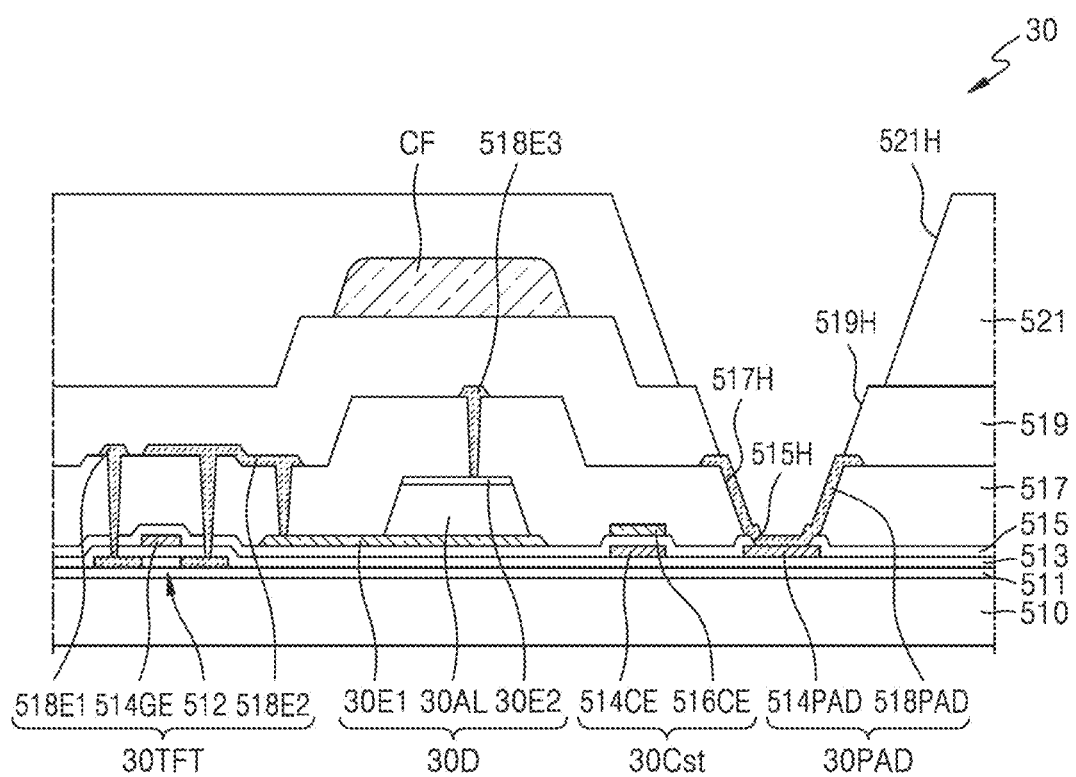
FIG. 7 is a cross-sectional view schematically illustrating a light detection layer according to an embodiment.

FIG. 7 is a cross-sectional view schematically illustrating a light detection layer 30 according to an embodiment.

Referring to FIG. 7, an embodiment of the light detection layer 30 may detect light reflected from a discoloration sensor layer. The light detection layer 30 may include a detection layer substrate 510, a detection layer thin-film transistor 30TFT, a photodiode 30D, a detection layer capacitor 30Cst, a detection layer pad 30PAD, a color filter CF. In such an embodiment, the light detection layer 30 may further include a detection buffer layer 511, a first insulating layer 513, a second insulating layer 515, a third insulating layer 517, a fourth insulating layer 519, and a planarization layer 521.

The detection layer substrate 510 may include an insulating substrate or an insulating film including an insulating material such as a glass material, a metal material, or a polymer resin. In an embodiment, the detection layer substrate 510 may include glass or a polymer resin, such as polyethersulfone, polyarylate, polyetherimide, polyethylene naphthalate, polyethylene terephthalate, polyphenylene sulfide, polyimide, polycarbonate, cellulose triacetate, cellulose acetate propionate, or the like.

The detection buffer layer 511 may be disposed on the detection layer substrate 510. In an embodiment, the detection buffer layer 511 may include an inorganic insulating material such as silicon nitride ($SiN_x$), silicon oxynitride (SiON), and silicon oxide ($SiO_2$), and may have a single layer structure or a multi-layer structure, each layer including at least one selected from the above-described inorganic insulating materials. In an alternative embodiment, the detection buffer layer 511 may include an organic insulating material, or may include an inorganic insulating material and an organic insulating material. In an alternative embodiment, the detection buffer layer 511 may be omitted.

The detection layer thin-film transistor 30TFT, the photodiode 30D, the detection layer capacitor 30Cst, and the detection layer pad 30PAD may be disposed on the detection buffer layer 511. The detection layer thin-film transistor 30TFT may include a detection semiconductor layer 512, a detection gate electrode 514GE, a detection source electrode 518E1, and a detection drain electrode 518E2.

The detection semiconductor layer 512 may be disposed on the detection buffer layer 511. The detection semiconductor layer 512 may include polysilicon. In an embodiment, the detection semiconductor layer 512 may include amorphous silicon, may include an oxide semiconductor, or may include an organic semiconductor or the like. The detection semiconductor layer 512 may include a channel area, and a drain area and a source area respectively arranged at opposite sides of the channel area.

The first insulating layer 513 may be disposed on the detection buffer layer 511 to cover the detection semiconductor layer 512. The first insulating layer 513 may include an inorganic insulating material such as $SiO_2$, $SiN_x$, SiON, aluminum oxide ($Al_2O_3$), titanium oxide ($TiO_2$), tantalum oxide ($Ta_2O_5$), hafnium oxide ($HfO_2$), and/or zinc oxide (ZnO).

The detection gate electrode 514GE may be disposed on the first insulating layer 513 and may overlap the channel area of the detection semiconductor layer 512. The detection gate electrode 514GE may include a low-resistance metal material. The detection gate electrode 514GE may include a conductive material including molybdenum (Mo), aluminum (Al), copper (Cu), titanium (Ti), etc., and may be formed in a multi-layer or a single layer, each layer including at least one selected from the above-described materials.

The second insulating layer 515 may cover the detection gate electrode 514GE. The second insulating layer 515 may include $SiO_2$, $SiN_x$, SiON, $Al_2O_3$, $TiO_2$, $Ta_2O_5$, $HfO_2$, or ZnO. The second insulating layer 515 may include a single layer or a multi-layer, each layer including at least one selected from the above-described inorganic insulating materials.

The third insulating layer 517 may be disposed on the second insulating layer 515. The third insulating layer 517 may include $SiO_2$, $SiN_x$, SiON, $Al_2O_3$, $TiO_2$, $Ta_2O_5$, $HfO_2$, or ZnO. The third insulating layer 517 may include a single layer or a multi-layer, each layer including at least one selected from the above-described inorganic insulating materials.

The detection source electrode 518E1 and the detection drain electrode 518E2 may be disposed on the third insulating layer 517. Each of the detection source electrode 518E1 and the detection drain electrode 518E2 may be electrically connected to the detection semiconductor layer 512 through a contact hole defined in the first insulating layer 513, the second insulating layer 515 and the third insulating layer 517. The detection source electrode 518E1 and the detection drain electrode 518E2 may include a material having high conductivity. At least one of the detection source electrode 518E1 and the detection drain electrode 518E2 may include a conductive material including Mo, Al, Cu, or Ti, and include a single layer or a multi-layer, each layer including at least one selected from the above-described materials. In an embodiment, at least one of the detection source electrode 518E1 and the detection drain electrode 518E2 may have a multi-layer structure of a Ti layer, an Al layer, and another Ti layer (Ti/Al/Ti).

The photodiode 30D may receive light reflected from the discoloration sensor layer. In an embodiment, the photodiode 30D may receive light passed through the color filter CF. In an embodiment, the photodiode 30D may include a PIN photodiode. The photodiode 30D may include a first electrode 30E1, a photo semiconductor layer 30AL, and a second electrode 30E2.

The first electrode 30E1 may be electrically connected to the detection source electrode 518E1 or the detection drain electrode 518E2. In an embodiment, the first electrode 30E1 may be connected to the detection source electrode 518E1 or the detection drain electrode 518E2 through the contact hole defined in the third insulating layer 517. The first electrode 30E1 may include a material having high conductivity. In an embodiment, the first electrode 30E1 may include a conductive material including Mo, Al, Cu, or Ti, and may be a single layer or a multi-layer, each layer including at least one selected from the above-described materials. In an embodiment, the first electrode 30E1 may have a multi-layer structure of a Ti layer, an Al layer, and another Ti layer.

The photo semiconductor layer 30AL may be disposed on the first electrode 30E1. In an embodiment, the photo semiconductor layer 30AL may include an intrinsic semiconductor. A current generated due to light incident on the photo semiconductor layer 30AL may flow between the first electrode 30E1 and the second electrode 30E2.

The second electrode 30E2 may be disposed on the photo semiconductor layer 30AL. The second electrode 30E2 may be a transparent electrode. In an embodiment, the second electrode 30E2 may include a conductive oxide such as indium tin oxide ("ITO"), indium zinc oxide ("IZO"), ZnO, $In_2O_3$, indium gallium oxide ("IGO"), or aluminum zinc oxide ("AZO").

A bias electrode 518E3 may be disposed on the third insulating layer 517. The bias electrode 518E3 may be electrically connected to the second electrode 30E2 through the contact hole defined in the third insulating layer 517. In an embodiment, the bias electrode 518E3 may include a same material as at least one selected from the bias electrode 518E3 and the detection drain electrode 518E2.

The detection layer capacitor 30Cst may include a first capacitor electrode 514CE and a second capacitor electrode 516CE. In an embodiment, the first capacitor electrode 514CE may be arranged between the first insulating layer 513 and the second insulating layer 515. In an embodiment, the first capacitor electrode 514CE may include a same material as the detection gate electrode 514GE. The second capacitor electrode 516CE may be arranged between the second insulating layer 515 and the third insulating layer 517, and may overlap the first capacitor electrode 514CE. The second capacitor electrode 516CE may include a same material as the first electrode 30E1.

The detection layer pad 30PAD may include a first pad 514PAD and a second pad 518PAD. The first pad 514PAD may be arranged between the first insulating layer 513 and the second insulating layer 515. The first pad 514PAD may be exposed by a hole 515H of the second insulating layer 515. The first pad 514PAD may include a same material as the detection gate electrode 514GE. The second pad 518PAD may be disposed on the first pad 514PAD and may overlap the first pad 514PAD. The second pad 518PAD may overlap the hole 515H of the second insulating layer 515 and a hole 517H of the third insulating layer 517. In an embodiment, the second pad 518PAD may include a same material as the bias electrode 518E3.

The fourth insulating layer 519 may be disposed on the third insulating layer 517 to cover the detection source electrode 518E1, the detection drain electrode 518E2, and the bias electrode 518E3. A hole 519H is defined through the fourth insulating layer 519, such that the second pad 518PAD is exposed therethrough. In an embodiment, the fourth insulating layer 519 may include $SiO_2$, $SiN_x$, SiON, $Al_2O_3$, $TiO_2$, $Ta_2O_5$, $HfO_2$, or ZnO. The fourth insulating layer 519 may include a single layer or a multi-layer, each layer including at least one selected from the above-described inorganic insulating materials.

The color filter CF may transmit light in a particular wavelength band. In an embodiment, the color filter CF may transmit light in a red wavelength band, light in a green wavelength band, or light in a blue wavelength band. The color filter CF may be disposed to overlap the photodiode 30D. In an embodiment, the color filter CF may be disposed on the fourth insulating layer 519.

The planarization layer 521 may be disposed on the color filter CF. The planarization layer 521 may have an approximately flat upper surface. In an embodiment, a hole 521H may be defined through the planarization layer 521 to expose the detection layer pad 30PAD. In an embodiment, the planarization layer 521 may include an organic material such as acryl, benzocyclobutene ("BCB"), hexamethyldisiloxane ("HMDSO"), or the like.

Figure 8:
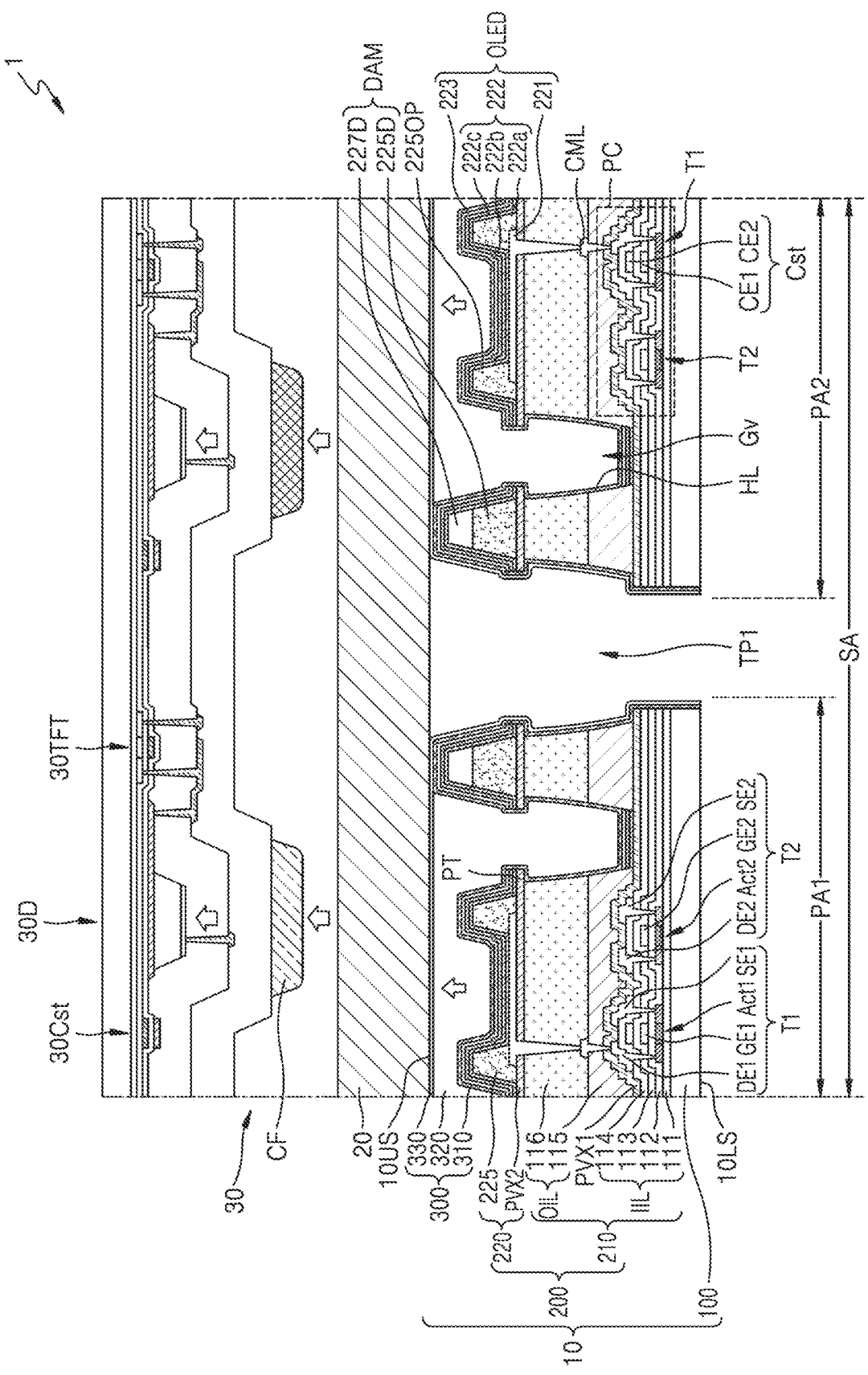
FIG. 8 is a cross-sectional view schematically illustrating a portion of a display device according to an embodiment.

FIG. 8 is a cross-sectional view schematically illustrating a portion of a display device 1 according to an embodiment. In FIG. 8, the same or like reference numerals as those of FIG. 2 denote the same or like elements, and thus, any repetitive detailed descriptions thereof will be omitted or simplified.

Referring to FIG. 8, an embodiment of the display device 1 may include a display panel 10, a discoloration sensor layer 20, and a light detection layer 30. The display panel 10 may include an upper surface 10US and a lower surface 10LS. In an embodiment, the lower surface 10LS of the display panel 10 may be a surface opposite to the upper surface 10US of the display panel 10.

The display panel 10 may include a sensor area SA exposed to a target material. The display panel 10 may include a first through portion TP1 in the sensor area SA. The first through portion TP1 may penetrate through the upper surface 10US and the lower surface 10LS of the display panel 10. In such an embodiment, elements of the display panel 10 may not be arranged in the first through portion TP1. The first through portion TP1 may overlap the discoloration sensor layer 20. Thus, at least a portion of the discoloration sensor layer 20 may be exposed.

In an embodiment, the sensor area SA may include a first pixel area PA1 and a second pixel area PA2 spaced apart from each other, and an edge of the first pixel area PA1 and an edge of the second pixel area PA2 may at least partially define the first through portion TP1 of the display panel 10.

The display panel 10 may include a substrate 100, a display layer 200, and an encapsulation layer 300. The display layer 200 may include a pixel circuit layer 210 and a display element layer 220.

The pixel circuit layer 210 may be disposed on the substrate 100. The pixel circuit layer 210 may include an inorganic insulating layer IIL, a first inorganic layer PVX1, an organic insulating layer OIL, and a pixel circuit PC. In an embodiment, the pixel circuit PC may include a driving thin-film transistor T1, a switching thin-film transistor T2, and a storage capacitor Cst. The driving thin-film transistor T1 may include a first semiconductor layer Act1, a first gate electrode GE1, a first source electrode SE1, and a first drain electrode DE1.

In an embodiment, the inorganic insulating layer IIL may be disconnected by the first through portion TP1 therebetween. In such an embodiment, in the sensor area SA, a portion of the inorganic insulating layer IIL may be apart from the other portion of the inorganic insulating layer IIL with the first through portion TP1 therebetween. In an embodiment, the inorganic insulating layer IIL may include a buffer layer 111, a first gate insulating layer 112, a second gate insulating layer 113, and an interlayer insulating layer 114.

The buffer layer 111 may be disposed on the substrate 100. In an embodiment, the buffer layer 111 may include an inorganic insulating material such as $SiN_x$, SiON, and $SiO_2$, and may have a single layer or a multi-layer, each layer including at least one selected from the above-described inorganic insulating materials.

The first semiconductor layer Act1 may be disposed on the buffer layer 111. In an embodiment, the first semiconductor layer Act1 may include polysilicon. In an alternative embodiment, the first semiconductor layer Act1 may include amorphous silicon, may include an oxide semiconductor, or may include an organic semiconductor or the like. The first semiconductor layer Act1 may include a channel area, and a drain area and a source area respectively arranged at opposite sides of the channel area.

The first gate electrode GE1 may overlap the channel area of the first semiconductor layer Act1. The first gate electrode GE1 may include a low-resistance metal material. The first gate electrode GE1 may include a conductive material such as Mo, Al, Cu, Ti, or the like, and may include a single layer or a multi-layer, each layer including at least one selected from the above-described materials.

The first gate insulating layer 112 between the first semiconductor layer Act1 and the first gate electrode GE1 may include an inorganic insulating material such as $SiO_2$, $SiN_x$, SiON, $Al_2O_3$, $TiO_2$, $Ta_2O_5$, $HfO_2$, and/or ZnO.

The second gate insulating layer 113 may cover the first gate electrode GE1. Similar to the first gate insulating layer 112, the second gate insulating layer 113 may include an inorganic insulating material such as $SiO_2$, $SiN_x$, SiON, $Al_2O_3$, $TiO_2$, $Ta_2O_5$, $HfO_2$, and/or ZnO.

An upper electrode CE2 of the storage capacitor Cst may be disposed on the second gate insulating layer 113. The upper electrode CE2 may overlap the first gate electrode GE1 thereunder. In such an embodiment, the first gate electrode GE1 of the driving thin-film transistor T1 and the upper electrode CE2 overlapping each other with the second gate insulating layer 113 therebetween may define the storage capacitor Cst. In such an embodiment, the first gate electrode GE1 of the driving thin-film transistor T1 may function as a lower electrode CE1 of the storage capacitor Cst.

In an embodiment, as described above, the storage capacitor Cst and the driving thin-film transistor T1 may overlap each other. In an alternative embodiment, the storage capacitor Cst may not overlap the driving thin-film transistor T1.

The upper electrode CE2 may include Al, platinum (Pt), palladium (Pd), silver (Ag), magnesium (Mg), gold (Au), nickel (Ni), neodymium (Nd), iridium (Ir), chrome (Cr), calcium (Ca), Mo, Ti, tungsten (Wo), and/or Cu, and may include a single layer or a multi-layer, each layer including at least one selected from the above-described materials.

The interlayer insulating layer 114 may cover the upper electrode CE2. The interlayer insulating layer 114 may include $SiO_2$, $SiN_x$, SiON, $Al_2O_3$, $TiO_2$, $Ta_2O_5$, $HfO_2$, and/or ZnO. The interlayer insulating layer 114 may include a single layer or a multi-layer, each layer including at least one selected from the above-described inorganic insulating materials.

The first drain electrode DE1 and the first source electrode SE1 may be disposed on the interlayer insulating layer 114. The first drain electrode DE1 and the first source electrode SE1 may be electrically connected to the first semiconductor layer Act1 through a contact hole defined in the first gate insulating layer 112, the second gate insulating layer 113, and the interlayer insulating layer 114. The first drain electrode DE1 and the first source electrode SE1 may include a material having high conductivity. The first drain electrode DE1 and the first source electrode SE1 may include a conductive material including Mo, Al, Cu, Ti, or the like, and may include a single layer or a multi-layer, each including at least one selected from the above-described conductive materials. In an embodiment, the first drain electrode DE1 and the first source electrode SE1 may have a multi-layer structure of a Ti layer, an Al layer, and another Ti layer.

The switching thin-film transistor T2 may include a second semiconductor layer Act2, a second gate electrode GE2, a second drain electrode DE2, and a second source electrode SE2. The second semiconductor layer Act2, the second gate electrode GE2, the second drain electrode DE2, and the second source electrode SE2 are similar to the first semiconductor layer Act1, the first gate electrode GE1, the first drain electrode DE1, and the first source electrode SE1, respectively, and thus, any repetitive detailed descriptions thereof will be omitted.

The organic insulating layer OIL may be disposed on the inorganic insulating layer K. In an embodiment, the organic insulating layer OIL may include a first organic insulating layer 115 and a second organic insulating layer 116. The first organic insulating layer 115 may cover the first drain electrode DE1 and the first source electrode SE1. The first organic insulating layer 115 may include an organic material. In one embodiment, for example, the first organic insulating layer 115 may include an organic insulating material including a general-purpose polymer such as polymethylmethacrylate ("PMMA") or polystyrene ("PS"), polymer derivatives having a phenol-based group, an acryl-based polymer, an imide-based polymer, an aryl ether-based polymer, an amide-based polymer, a fluorine-based polymer, a p-xylene-based polymer, a vinyl alcohol-based polymer, or any blends thereof.

A connection electrode CML may be disposed on the first organic insulating layer 115. In an embodiment, the connection electrode CML may be electrically connected to the first drain electrode DE1 or the first source electrode SE1 through a contact hole defined in the first organic insulating layer 115. The connection electrode CML may include a material having high conductivity. The connection electrode CML may include a conductive material including Mo, Al, Cu, Ti, or the like, and may include a multi-layer or a single layer, each layer including at least one selected from the above-described conductive materials. In an embodiment, the connection electrode CML may have a multi-layer structure of a Ti layer, an Al layer, and another Ti layer.

The second organic insulating layer 116 may cover the connection electrode CML. The second organic insulating layer 116 may include an organic material. The second organic insulating layer 116 may include an organic material such as a general-purpose polymer such as PMMA or PS, a polymer derivative having a phenol-based group, or an acryl-based polymer, an imide-based polymer, an aryl-ether-based polymer, an amide-based polymer, a fluorine-based polymer, a p-xylene-based polymer, a vinyl alcohol-based polymer, or any blends thereof.

In an embodiment, a hole HL may be defined in the organic insulating layer OIL in the sensor area SA. The hole HL, which is a display element, may be arranged between an organic light-emitting diode OLED and the first through portion TP1. In an embodiment, the hole HL may penetrate through the organic insulating layer OIL. The hole HL may be provided by overlapping a hole of the first organic insulating layer 115 and a hole of the second organic insulating layer 116. In an alternative embodiment, the hole HL may be provided in the second organic insulating layer 116. In such an embodiment, an upper surface of the first organic insulating layer 115 may be exposed by the hole HL in the second organic insulating layer 116. Hereinafter, embodiments where the hole HL is provided in the first organic insulating layer 115 and the second organic insulating layer 116 will be described in detail.

In an alternative embodiment, the organic insulating layer OIL may have a recess engraved in a thickness direction of the organic insulating layer OIL, instead of the hole HL.

In an embodiment, the first inorganic layer PVX1 may be arranged between the interlayer insulating layer 114 and the first organic insulating layer 115. The first inorganic layer PVX1 may cover the first source electrode SE1, the first drain electrode DE1, the second source electrode SE2, and the second drain electrode DE2. In an embodiment, a contact hole may be defined in the first inorganic layer PVX1 so that the first source electrode SE1 or the first drain electrode DE1 is electrically connected to the connection electrode CML.

In an alternative embodiment, the first inorganic layer PVX1 may be arranged between the first organic insulating layer 115 and the second organic insulating layer 116. In such an embodiment, the first inorganic layer PVX1 may cover the connection electrode CML.

At least a portion of the first inorganic layer PVX1 may be exposed by the hole HL. The first inorganic layer PVX1 may include a single layer or a multi-layer, each layer including an inorganic material such as $SiN_x$ and/or $SiO_2$. In an alternative embodiment, the first inorganic layer PVX1 may be omitted.

The display element layer 220 may be disposed on the pixel circuit layer 210. The display element layer 220 may include the organic light-emitting diode OLED as a display element. In an embodiment, the organic light-emitting diode OLED may be provided plural in the sensor area SA. A plurality of organic light-emitting diodes OLED may be arranged in the first pixel area PA1 and the second pixel area PA2. The plurality of organic light-emitting diodes OLED may be apart from each other with the first through portion TP1 therebetween. The organic light-emitting diode OLED may include a pixel electrode 221, an intermediate layer 222, and an opposite electrode 223.

In an embodiment, the pixel electrode 221 may include a conductive oxide such as ITO, IZO, ZnO, $In_2O_3$, indium IGO, or AZO. In an alternative embodiment, the pixel electrode 221 may include a reflective layer including Ag, Mg, Al, Pt, Pd, Au, Ni, Nd, Ir, Cr, or any compounds thereof. In another alternative embodiment, the pixel electrode 221 may further include a layer including ITO, IZO, ZnO, or $In_2O_3$ on/under the reflective layer.

A pixel-defining layer 225 with an opening 2250P defined therein to expose a central portion of the pixel electrode 221 may be disposed on the pixel electrode 221. The pixel-defining layer 225 may include an organic insulating material and/or an inorganic insulating material. The opening 2250P may define an emission area of light emitted by the organic light-emitting diode OLED. In one embodiment, for example, a width of the opening 2250P may correspond to a width of the emission area. In an embodiment, a spacer may be disposed on the pixel-defining layer 225.

The intermediate layer 222 may be disposed on the pixel-defining layer 225. The intermediate layer 222 may include an emission layer 222b in the opening 2250P of the pixel-defining layer 225. The emission layer 222b may include a polymer or low-molecular weight organic material emitting light of a color.

A first functional layer 222a and a second functional layer 222c may be disposed on and under the emission layer 222b, respectively. In one embodiment, for example, the first functional layer 222a may include a hole transport layer ("HTL"), or may include an HTL and a hole injection layer ("HIL"). The second functional layer 222c is an element disposed on the emission layer 212b, and may be optional. The second functional layer 222c may include an electron transport layer ("ETL") and/or an electron injection layer ("EIL"). Like the opposite electrode 223 to be described later, the first functional layer 222a and/or the second functional layer 222c may be common layers entirely covering the substrate 100.

The opposite electrode 223 may include a conductive material having a low work function. In one embodiment, for example, the opposite electrode 223 may include a (semi)transparent layer including Ag, Mg, Al, Pt, Pd, Au, Ni, Nd, Ir, Cr, Li, Ca, or any alloys thereof. In an embodiment, the opposite electrode 223 may further include a layer such as an ITO layer, an IZO layer, a ZnO layer, or an $In_2O_3$ layer on the (semi)transparent layer including the above-described materials.

In an embodiment, a capping layer (not shown) may be further disposed on the opposite electrode 223. The capping layer may include lithium fluoride (LiF), an inorganic material, and/or an organic material.

A second inorganic layer PVX2 may be arranged between the organic light-emitting diode OLED and the second organic insulating layer 116. In such an embodiment, the organic light-emitting diode OLED may be disposed on the second inorganic layer PVX2. The second inorganic layer PVX2 may include a plurality of inorganic patterns apart from one another on the second organic insulating layer 116. The second inorganic layer PVX2 may have a protruding tip PT protruding in a direction toward a center direction of the hole HL. Thus, a lower surface of the protruding tip PT may be exposed through the hole HL. In such an embodiment, the hole HL may have an undercut structure. The second inorganic layer PVX2 may include a single layer or a multi-layer, each layer including an inorganic material such as $SiN_x$ and/or $SiO_2$.

In an embodiment, the first inorganic layer PVX1, the hole HL, and the second inorganic layer PVX2 may define a groove Gv in the sensor area SA. In an alternative embodiment, the organic insulating layer OIL has a recess, and the recess and the second inorganic layer PVX2 may define the groove Gv in the sensor area SA.

The hole HL and the protruding tip PT of the second inorganic layer PVX2 may have a structure for disconnecting the first functional layer 212a and the second functional layer 212c from each other. In an embodiment, the first functional layer 222a, the second functional layer 222c, and the opposite electrode 223 may be formed over an entire surface of the substrate 100. In such an embodiment, the first functional layer 222a and the second functional layer 222c may include an organic material, and external oxygen, moisture, or the like may flow into the organic light-emitting diode OLED through at least one of the first functional layer 222a and the second functional layer 222c. Such oxygen or moisture may cause damage to the organic light-emitting diode OLED. The hole HL and the protruding tip PT of the second inorganic layer PVX2 may disconnect the first functional layer 222a and the second functional layer 222c from each other, and a first functional layer pattern and a second functional layer pattern may be arranged inside the hole HL. Thus, moisture or oxygen may be prevented from flowing into the organic light-emitting diode OLED from the first through portion TP1, thereby preventing or reducing damage to the organic light-emitting diode OLED. However, a structure in which the first functional layer 222a and the second functional layer 222c are disconnected is not limited thereto, and various structures of disconnecting the first functional layer 222a and the second functional layer 222c from each other may be employed in the display panel 10.

A dam portion DAM may be disposed on the second inorganic layer PVX2. The dam portion DAM may protrude in a thickness direction of the substrate 100 from the second inorganic layer PVX2. The dam portion DAM may be arranged adjacent to the first through portion TP1. The dam portion DAM may be closer to the first through portion TP1 than the hole HL. The dam portion DAM may include a pattern layer 225D and an upper pattern layer 227D. In an embodiment, the pattern layer 225D may include a same material as the pixel-defining layer 225. The upper pattern layer 227D may include an organic insulating material and/or an inorganic insulating material.

The encapsulation layer 300 may cover the organic light-emitting diode OLED. The encapsulation layer 300 may be disposed on the opposite electrode 223. The encapsulation layer 300 may be divided with the first through portion TP1 therebetween. The encapsulation layer 300 may be disposed on the opposite electrode 223. In an embodiment, the encapsulation layer 300 may include at least one inorganic encapsulation layer and at least one organic encapsulation layer. In an embodiment, as shown in FIG. 8, the encapsulation layer 300 includes a first inorganic encapsulation layer 310, an organic encapsulation layer 320, and a second inorganic encapsulation layer 330, which are sequentially stacked one on another.

The first inorganic encapsulation layer 310 may cover the organic light-emitting diode OLED. The first inorganic encapsulation layer 310 may entirely and continuously cover the substrate 100. The first inorganic encapsulation layer 310 may cover a plurality of organic light-emitting diodes OLED, the hole HL, and the dam portion DAM. The first inorganic encapsulation layer 310 may contact the protruding tip PT of the second inorganic layer PVX2. The first inorganic encapsulation layer 310 may contact the first inorganic layer PVX1. Thus, moisture or oxygen may be prevented from flowing into the organic light-emitting diode OLED from the first through portion TP1 through a layer including an organic material. In an embodiment, the first inorganic encapsulation layer 310 may be separated with respect to the first through portion TP1.

The organic encapsulation layer 320 may be disposed on the first inorganic encapsulation layer 310. The organic encapsulation layer 320 may overlap the organic light-emitting diode OLED, and the organic encapsulation layer 320 may fill the hole HL. In an embodiment, the organic encapsulation layer 320 may be separated with respect to the first through portion TP1. The dam portion DAM protrudes in the thickness direction of the substrate 100 from an upper surface of the second inorganic layer PVX2, and thus, a flow of the organic encapsulation layer 320 may be controlled.

The second inorganic encapsulation layer 330 may cover the organic encapsulation layer 320. The second inorganic encapsulation layer 330 may entirely and continuously cover the substrate 100. The second inorganic encapsulation layer 330 may contact the first inorganic encapsulation layer 310 on the dam portion DAM. Thus, the organic encapsulation layer 320 may be separated by the dam portion DAM. In addition, the second inorganic encapsulation layer 330 may be separated with respect to the first through portion TP1.

The first inorganic encapsulation layer 310 and the second inorganic encapsulation layer 330 may include at least one inorganic material selected from among $Al_2O_3$, $TiO_2$, $Ta_2O_5$, $HfO_2$, $ZnO$, $SiO_2$, $SiN_x$, and $SiON$. The organic encapsulation layer 320 may include a polymer-based material. The polymer-based material may include an acryl-based resin, an epoxy-based resin, polyimide, polyethylene, or the like. In an embodiment, the organic encapsulation layer 320 may include acrylate.

The discoloration sensor layer 20 may be arranged in the sensor area SA. In an embodiment, the discoloration sensor layer 20 may be disposed on the upper surface 10US of the display panel 10. Thus, light emitted by the organic light-emitting diode OLED may be incident on the discoloration sensor layer 20.

The discoloration sensor layer 20 may overlap the first through portion TP1. The discoloration sensor layer 20 may be exposed by the first through portion TP1. Thus, a target material may reach the discoloration sensor layer 20 through the first through portion TP1. In an embodiment, the target material may be in a gaseous state.

The discoloration sensor layer 20 may be discolored when exposed to the target material. In an embodiment, the discoloration sensor layer 20 may include an M13 bacteriophage. In such an embodiment, the M13 bacteriophage may overlap the sensor area SA. When the M13 bacteriophage is exposed to the target material, an arrangement of M13 bacteriophage bundles may be changed.

The light detection layer 30 may be disposed on the discoloration sensor layer 20. The light detection layer 30 may face the upper surface 10US of the display panel 10. The light detection layer 30 may include a detection layer substrate, a detection layer thin-film transistor 30TFT, a photodiode 30D, a detection layer capacitor 30Cst, and a color filter CF. In an embodiment, the color filter CF may be arranged between the photodiode 30D and the display panel 10.

The light detection layer 30 may detect light. The photodiode 30D may receive light reflected from the discoloration sensor layer 20. In an embodiment, the photodiode 30D may receive light via the color filter CF. Thus, the photodiode 30D may detect discoloration of the discoloration sensor layer 20. In one embodiment, for example, light having a reference wavelength band in the organic light-emitting diode OLED may be incident on the discoloration sensor layer 20. Before the discoloration sensor layer 20 is exposed to the target material, the discoloration sensor layer 20 may reflect light having a first wavelength band from among light having a reference wavelength band. When the discoloration sensor layer 20 is exposed to the target material, the discoloration sensor layer 20 may reflect light having a second wavelength band. In this case, the color filter CF is arranged between the photodiode 30D and the discoloration sensor layer 20, each of the photodiodes 30D may detect a color change. Thus, the light detection layer 30 may obtain information on whether the target material is present.

Figure 9:
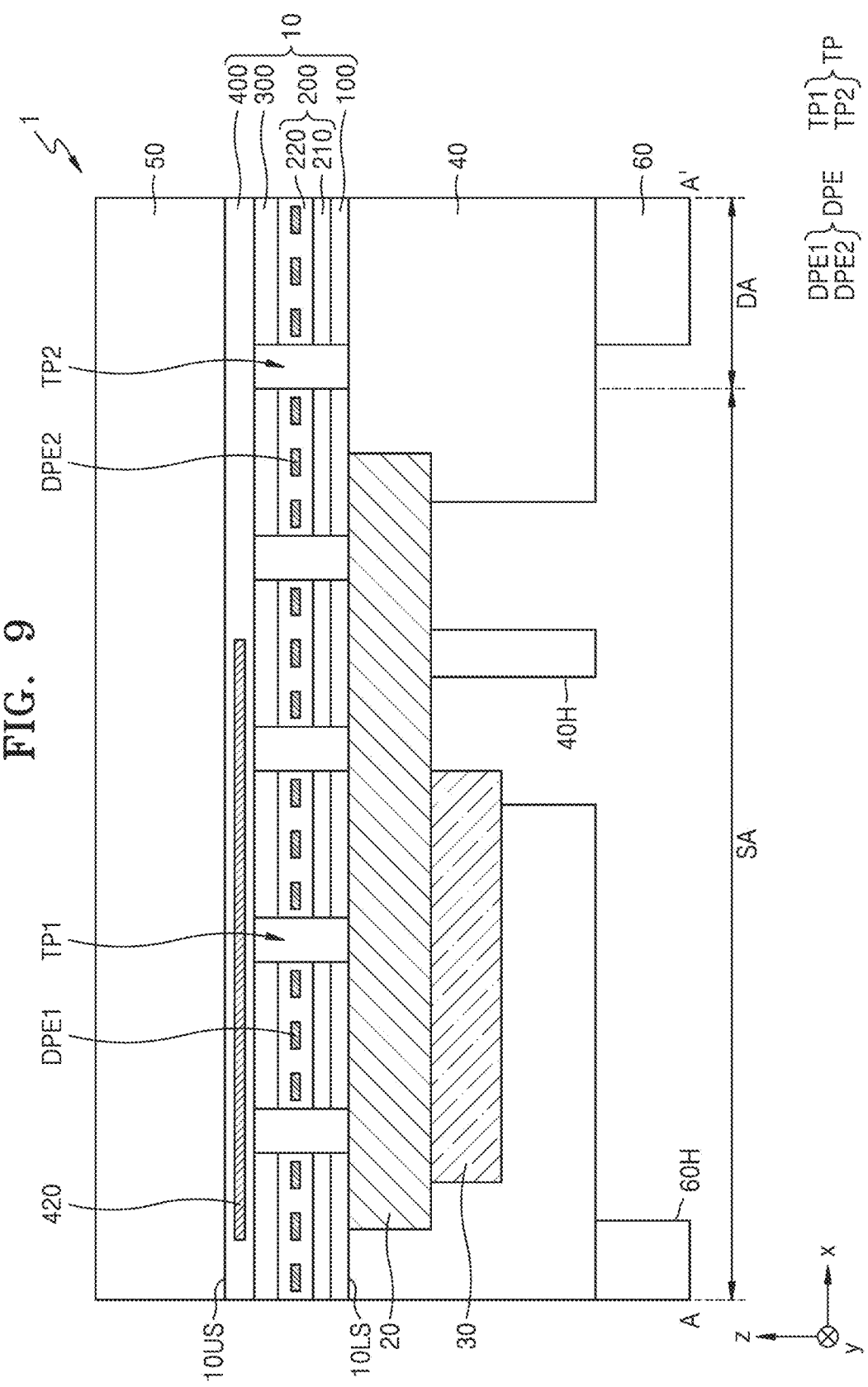
FIG. 9 is a cross-sectional view schematically illustrating a display device according to an alternative embodiment.

FIG. 9 is a cross-sectional view schematically illustrating a display device 1 according to an alternative embodiment. FIG. 9 is a cross-sectional view illustrating the display device 1 in FIG. 1A, taken along line A-A'. In FIG. 9, the same or like reference numerals as those of FIG. 2 denote the same or like elements, and thus, any repetitive detailed descriptions thereof will be omitted or simplified.

Referring to FIG. 9, an embodiment of the display device 1 may include the display panel 10, a discoloration sensor layer 20, a light detection layer 30, a lower cover 40, an upper cover 50, and an adhesive layer 60.

The display panel 10 may include an upper surface 10US and a lower surface 10LS. In an embodiment, the lower surface 10LS of the display panel 10 may be a surface opposite to the upper surface 10US of the display panel 10. In an embodiment, the lower cover 40 may be disposed on the lower surface 10LS of the display panel 10. The upper cover 50 may be disposed on the upper surface 10US of the display panel 10.

The display panel 10 may include a sensor area SA and a display area DA. The sensor area SA may include an area exposed to a target material. The display panel 10 may display an image in the display area DA.

The display panel 10 may include a through portion TP. The through portion TP may be defined through the display panel 10 from the upper surface 10US to the lower surface 10LS of the display panel 10. The through portion TP may include a first through portion TP1 and a second through portion TP2. The first through portion TP1 may overlap the sensor area SA. The first through portion TP1 may overlap the discoloration sensor layer 20.

The display panel 10 may include a substrate 100, a display layer 200, an encapsulation layer 300, and a touch electrode layer 400. The touch electrode layer 400 may be disposed on the encapsulation layer 300. The touch electrode layer 400 may obtain coordinate information according to an external input, for example, a touch event. The touch electrode layer 400 may sense a touch using a mutual capacitance method, or the touch electrode layer 400 may sense a touch using a self-capacitance method.

In an embodiment, the touch electrode layer 400 may include a light reflection layer 420. The light reflection layer 420 may reflect light emitted by a display element DPE. In an embodiment, the light reflection layer 420 may overlap the sensor area SA and may be disposed on a display element layer 220. In an embodiment, the light reflection layer 420 may overlap the first through portion TP1. In an alternative embodiment, the light reflection layer 420 may be separated with respect to the first through portion TP1.

In an embodiment, as shown in FIG. 9, the light reflection layer 420 is included in the touch electrode layer 400, but not being limited thereto. In an alternative embodiment, the light reflection layer 420 may be independent from the touch electrode layer 400. In an embodiment, the light reflection layer 420 may include a metal.

The discoloration sensor layer 20 may be arranged in the sensor area SA. In an embodiment, the discoloration sensor layer 20 may be disposed on any of the upper surface 10US of the display panel 10 and the lower surface 10LS of the display panel 10. In one embodiment, for example, the discoloration sensor layer 20 may be disposed on the lower surface 10LS of the display panel 10. The discoloration sensor layer 20 may overlap the first through portion TP1. In an embodiment, the discoloration sensor layer 20 may overlap a plurality of first through portions TP1.

In an embodiment, the discoloration sensor layer 20 may include an M13 bacteriophage. In such an embodiment, the M13 bacteriophage may overlap the sensor area SA. When the M13 bacteriophage is exposed to a target material, an arrangement of M13 bacteriophage bundles may be changed.

The light detection layer 30 may be arranged in the sensor area SA. In an embodiment, the light detection layer 30 may be arranged under the discoloration sensor layer 20. In an embodiment, the light detection layer 30 may face the lower surface 10LS of the display panel 10. The discoloration sensor layer 20 may be arranged between the light detection layer 30 and the display panel 10.

The lower cover 40 may be arranged under the display panel 10. In an embodiment, the lower cover 40 may face the lower cover 40 of the display panel 10. The lower cover 40 may be disposed on the lower surface 10LS of the display panel 10. In an embodiment, the lower cover 40 may cover the discoloration sensor layer 20 and the light detection layer 30. In such an embodiment, the discoloration sensor layer 20 and the light detection layer 30 may be arranged between the display panel 10 and the lower cover 40.

The lower cover 40 may include a lower hole 40H. In an embodiment, the lower hole 40H may overlap the discoloration sensor layer 20. The lower hole 40H may expose the discoloration sensor layer 20. Thus, the target material may reach the discoloration sensor layer 20 through the lower hole 40H.

In an embodiment, the discoloration sensor layer 20 may be exposed via the lower hole 40H of the lower cover 40. When the target material reaches the discoloration sensor layer 20, the discoloration sensor layer 20 may be discolored. In an embodiment, the target material may be in a gaseous state or a liquid state. In one embodiment, for example, the target material may be a user's sweat or a material included in the sweat. The first display element DPE1 may be arranged in the sensor area SA of the display panel 10. A first display element DPE1 may irradiate light toward the light reflection layer 420, and the light reflection layer 420 may reflect the light so that the reflected light is incident on the discoloration sensor layer 20. In an embodiment, the light reflected on the light reflection layer 420 may be incident on the discoloration sensor layer 20 through the first through portion TP1 having a relatively high transmittance. Thus, light emitted by the first display element DPE1 may be incident on the discoloration sensor layer 20 with relatively little loss.

The light detection layer 30 may detect a color change of the discoloration sensor layer 20. Thus, the light detection layer 30 may obtain information on the color change, and the controller may determine whether the target material is present based on the information. In an embodiment, the controller may control the display panel 10 to display a diagnosis result in the display area DA. In an embodiment, as described above, the display device 1 may detect the target material even if the target material is in a liquid state.

Figure 10:
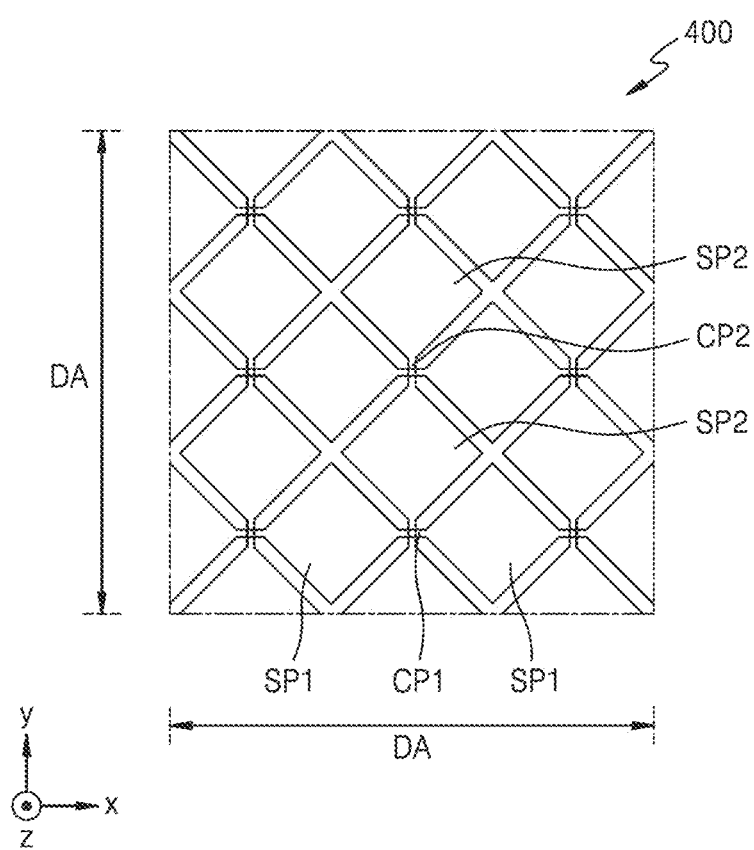
FIG. 10 is a plan view schematically illustrating a touch electrode layer according to an embodiment.
Figure 11:
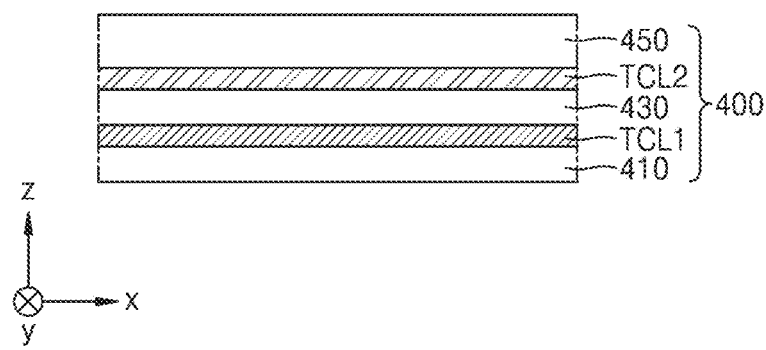
FIG. 11 is a cross-sectional view schematically illustrating a touch electrode layer according to an embodiment.

FIG. 10 is a plan view schematically illustrating a touch electrode layer 400 according to an embodiment. FIG. 11 is a cross-sectional view schematically illustrating the touch electrode layer 400 according to an embodiment.

Referring to FIG. 10, the touch electrode layer 400 may include a plurality of first sensing electrodes SP1 arranged in a first direction (for example, an x direction or a −x direction), and a plurality of second sensing electrodes SP2 arranged in a second direction (for example, a y direction or a −y direction).

A plurality of first sensing electrodes SP1 adjacent to each other may be electrically connected to each other through a first connection electrode CP1. A plurality of second sensing electrodes SP2 adjacent to each other may be electrically connected to each other through a second connection electrode CP2.

Referring to FIG. 11, the touch electrode layer 400 may include a first touch insulating layer 410, a first touch conductive layer TCL1, a second touch insulating layer 430, a second touch conductive layer TCL2, and a third touch insulating layer 450. The first touch insulating layer 410, the first touch conductive layer TCL1, the second touch insulating layer 430, the second touch conductive layer TCL2, and the third touch insulating layer 450 may be sequentially stacked one on another. In an embodiment, the touch electrode layer 400 may further include a light reflection layer 420 (see FIG. 9) in a sensor area. The light reflection layer 420 may be integrally provided as a single body with the first touch conductive layer TCL1. In an alternative embodiment, the touch electrode layer 400 is arranged in the sensor area, and may further include an upper light reflection layer integrally provided as a single unitary body with the second touch conductive layer TCL2.

The first touch conductive layer TCL1 or the second touch conductive layer TCL2 may include a metal layer or a transparent conductive layer. The metal layer may include Mo, mendelevium (Md), Ag, Ti, Cu, Al, and any alloys thereof. The transparent conductive layer may include a transparent conductive oxide such as ITO, IZO, ZnO, indium tin zinc oxide ("ITZO"), or the like. In an embodiment, the transparent conductive layer may include a conductive polymer such as poly(3,4-ethylenedioxythiophene) ("PEDOT"), a metal nanowire, graphene, or the like.

At least one selected from the first touch conductive layer TCL1 and the second touch conductive layer TCL2 may include a single layer or a multi-layer. At least one selected from the first touch conductive layer TCL1 as a single layer and the second touch conductive layer TCL2 as a single layer may include any of the metal layer and the transparent conductive layer.

In an embodiment, at least one selected from the first touch conductive layer TCL1 and the second touch conductive layer TCL2 may be defined by a single metal layer. In an alternative embodiment, at least one selected from the first touch conductive layer TCL1 and the second touch conductive layer TCL2 may be defined by a metal layer having a multi-layer structure. In one embodiment, for example, the multi-layered metal layer may have a structure in which a Ti layer, an Al layer, and another Ti layer are sequentially stacked, or may have a structure in which a Mo layer and a Md layer are sequentially stacked. In an embodiment, the multi-layered metal layer may include a metal layer and a transparent conductive layer.

In an embodiment, the first touch conductive layer TCL1 and the second touch conductive layer TCL2 may have different stacked structures or a same stacked structure. In one embodiment, for example, the first touch conductive layer TCL1 may include a metal layer, and the second touch conductive layer TCL2 may include a transparent conductive layer. In an alternative embodiment, the first touch conductive layer TCL1 and the second touch conductive layer TCL2 may include a same metal layer as each other.

In an embodiment, at least one selected from the first touch insulating layer 410, the second touch insulating layer 430, and the third touch insulating layer 450 may include a single layer or a multi-layer including an inorganic material such as $SiN_x$, $SiO_2$, and/or SiON. In an alternative embodiment, at least one selected from the first touch insulating layer 410, the second touch insulating layer 430, and the third touch insulating layer 450 may include an organic material.

Referring to FIGS. 10 and 11, in an embodiment, the first touch conductive layer TCL1 may include the first connection electrode CP1. The second touch conductive layer TCL2 may include a first sensing electrode SP1, a second sensing electrode SP2, and a second connection electrode CP2. In an alternative embodiment, the first touch conductive layer TCL1 may include the first sensing electrode SP1, the second sensing electrode SP2, and the first connection electrode CP1. In another alternative embodiment, the first touch conductive layer TCL1 may include the first sensing electrode SP1 and the first connection electrode CP1, and the second touch conductive layer TCL2 may include the second sensing electrode SP2 and the second connection electrode CP2. In such an embodiment, the first sensing electrode SP1 and the first connection electrode CP1 may be integrally provided as a single unitary body, and the second sensing electrode SP2 and the second connection electrode CP2 may be integrally formed as a single unitary body.

A material of the first touch conductive layer TCL1, a material of the second touch conductive layer TCL2, and an arrangement of the first sensing electrode SP1 and the second sensing electrode SP2 provided in the first touch conductive layer TCL1 and the second touch conductive layer TCL2 may be determined considering a sensing sensitivity. A resistor-capacitor ("RC") delay may affect the sensing sensitivity, and thus, an RC value may decrease because the first sensing electrode SP1 and the second sensing electrode SP2 included in a metal layer has a lower resistance than a transparent conductive layer. Thus, a charging time of a capacitance defined between the first sensing electrode SP1 and the second sensing electrode SP2 may be reduced. The first sensing electrode SP1 and the second sensing electrode SP2 included in the transparent conductive layer is not visible to a user compared to those included in the metal layer, and thus, an input area and a capacitance may increase.

Figure 12:
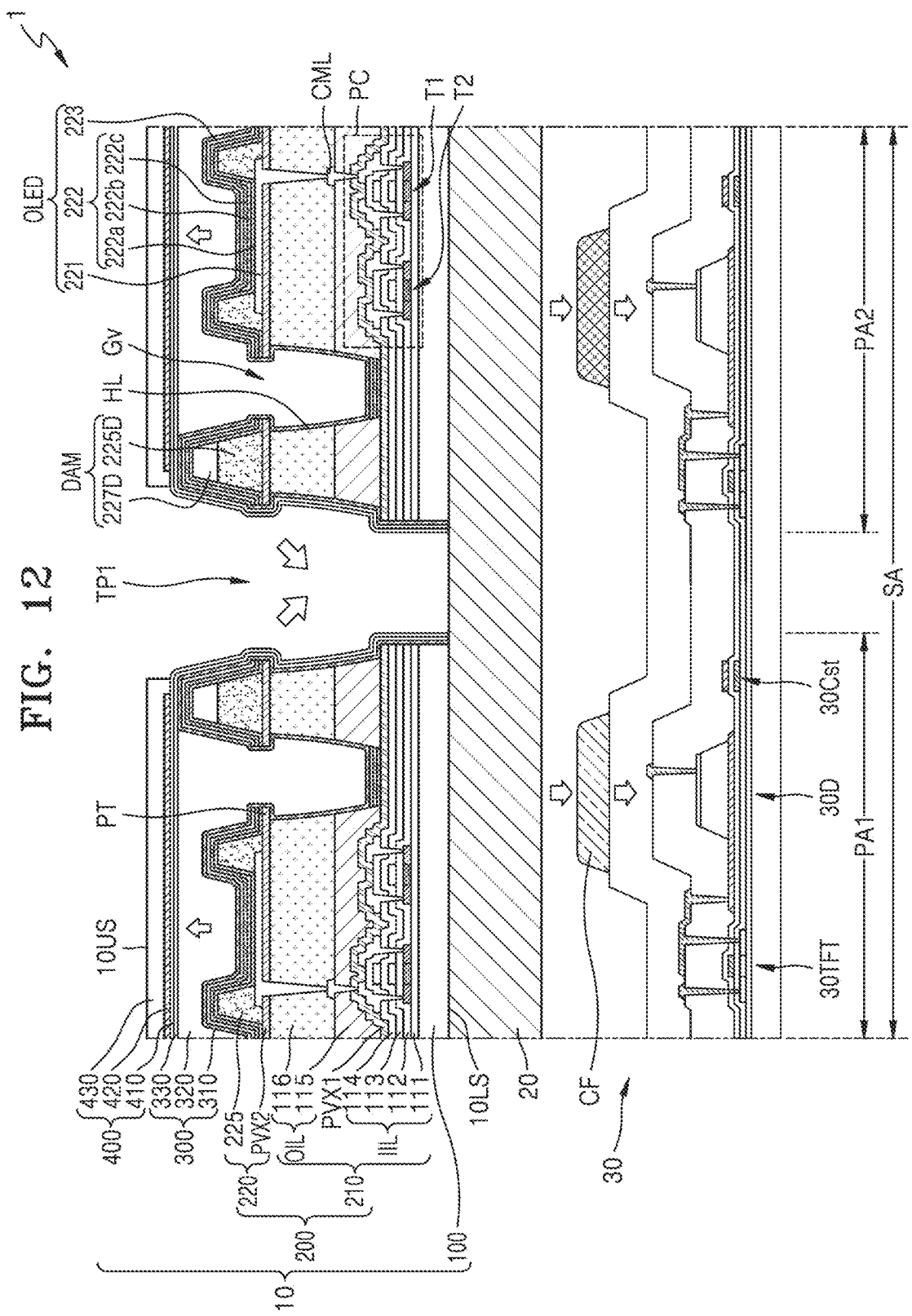
FIG. 12 is a cross-sectional view schematically illustrating a portion of a display device according to an alternative embodiment.

FIG. 12 is a cross-sectional view schematically illustrating a portion of a display device 1 according to an alternative embodiment. In FIG. 12, the same or like reference numerals as those of FIG. 8 denote the same or like elements, and thus, any repetitive detailed descriptions thereof will be omitted or simplified.

Referring to FIG. 12, an embodiment of the display device 1 may include a display panel 10, a discoloration sensor layer 20, and a light detection layer 30. The display panel 10 may include an upper surface 10US and a lower surface 10LS. In an embodiment, the lower surface 10LS of the display panel 10 may be a surface opposite to the upper surface 10US of the display panel 10.

The display panel 10 may include a sensor area SA exposed to a target material. The display panel 10 may include a first through portion TP1 in the sensor area SA. The first through portion TP1 may be defined through the display panel 10 from the upper surface 10US to the lower surface 10LS. The first through portion TP1 may not include elements of the display panel 10 arranged therein. The first through portion TP1 may overlap the discoloration sensor layer 20.

In an embodiment, the sensor area SA may include a first pixel area PA1 and a second pixel area PA2 spaced apart from each other, and an edge of the first pixel area PA1 and an edge of the second pixel area PA2 may at least partially define the first through portion TP1 of the display panel 10.

The display panel 10 may include a substrate 100, a display layer 200, an encapsulation layer 300, and a touch electrode layer 400, and the touch electrode layer 400 may be disposed on the encapsulation layer 300. In an embodiment, in the sensor area SA, the touch electrode layer 400 may include a first touch insulating layer 410, a light reflection layer 420, and a second touch insulating layer 430.

The first touch insulating layer 410 may be disposed on a second inorganic encapsulation layer 330. In an embodiment, the first touch insulating layer 410 may be arranged along a shape of the second inorganic encapsulation layer 330. In an alternative embodiment, the first touch insulating layer 410 may be omitted.

The light reflection layer 420 may be disposed on the first touch insulating layer 410. In an embodiment, the light reflection layer 420 may be separated with respect to the first through portion TP1. In an embodiment, the light reflection layer 420 may include a conductive material, for example, a metal. In an embodiment, the light reflection layer 420 may include Mo, Al, Cu, Ti, or the like, and may include a multi-layer or a single layer, each layer including at least one selected from the above-described conductive materials. In an embodiment, the light reflection layer 420 may have a structure in which a Ti layer, an Al layer, and another Ti layer are sequentially stacked.

Although not shown, in a display area, the first touch insulating layer TCL1 (see FIG. 11) may be disposed on the first touch insulating layer 410. In an embodiment, the first touch conductive layer TCL1 may be integrally formed as a single unitary body with the light reflection layer 420. The first touch conductive layer TCL1 may include a same material as the light reflection layer 420.

The second touch insulating layer 430 may be disposed on the light reflection layer 420. In an embodiment, the touch electrode layer 400 may further include an upper light reflection layer on the second touch insulating layer 430, the upper light reflection layer including a same material as the second touch conductive layer TCL2 (see FIG. 11). The upper light reflection layer may be arranged in the sensor area SA. In an embodiment, the second touch conductive layer TCL2 may be integrally provided as a single unitary body with the upper light reflection layer.

The discoloration sensor layer 20 may be arranged in the sensor area SA. In an embodiment, the discoloration sensor layer 20 may be disposed on the lower surface 10LS of the display panel 10. The discoloration sensor layer 20 may overlap the first through portion TP1.

In an embodiment, the discoloration sensor layer 20 may include an M13 bacteriophage. In such an embodiment, the M13 bacteriophage may overlap the sensor area SA. When the M13 bacteriophage is exposed to a target material, the arrangement of bundles of M13 bacteriophage may be changed.

The light detection layer 30 may be arranged in the sensor area SA. In an embodiment, the light detection layer 30 may be arranged under the discoloration sensor layer 20. In an embodiment, the light detection layer 30 may face the lower surface 10LS of the display panel 10. The discoloration sensor layer 20 may be arranged between the light detection layer 30 and the display panel 10.

The light detection layer 30 may detect light. In an embodiment, a photodiode 30D may receive light reflected from the discoloration sensor layer 20. In an embodiment, the color filter CF may be arranged between the display panel 10 and the photodiode 30D, and the photodiode 30D may receive light that passes through the color filter CF. Thus, the photodiode 30D may detect discoloration of the discoloration sensor layer 20.

When the target material reaches the discoloration sensor layer 20, the discoloration sensor layer 20 may be discolored. In an embodiment, the target material may be in a gaseous state or a liquid state. An organic light-emitting diode OLED may be arranged in the sensor area SA of the display panel 10. The organic light-emitting diode OLED may irradiate light toward the light reflection layer 420, and the light reflection layer 420 may reflect the light and allow the reflected light to be incident on the discoloration sensor layer 20. In an embodiment, the light reflected on the light reflection layer 420 may be incident on the discoloration sensor layer 20 through the first through portion TP1 having a relatively high transmittance. Thus, light emitted by the organic light-emitting diode OLED may be incident on the discoloration sensor layer 20 with relatively little light loss.

The light detection layer 30 may detect a color change of the discoloration sensor layer 20. Thus, the display device 1 may detect the target material. In such an embodiment, the display device 1 may obtain information on whether the target material is present, even when the target material is in a liquid state.

Figure 13:
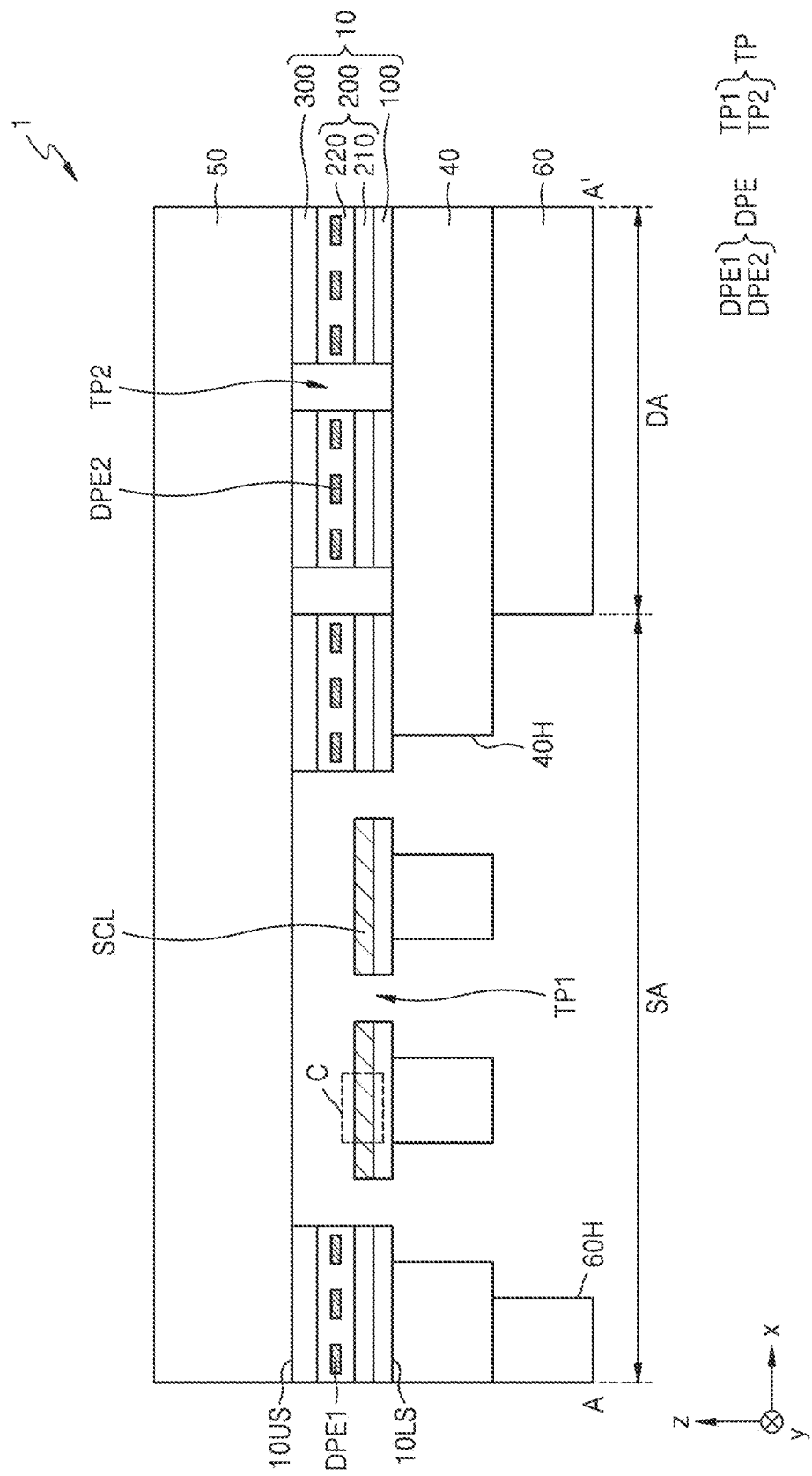
FIG. 13 is a cross-sectional view schematically illustrating a display device according to an alternative embodiment.
Figure 14:
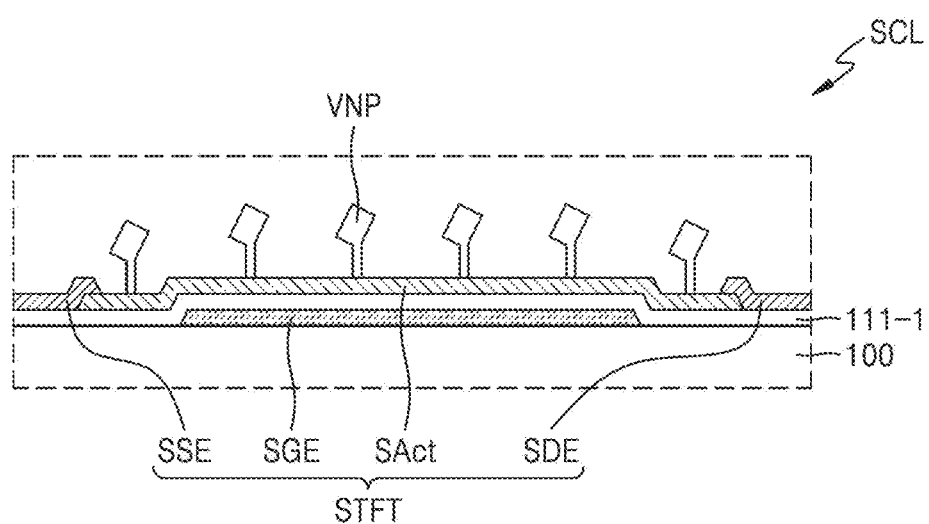
FIG. 14 is an enlarged view of a portion of the display device in FIG. 13.

FIG. 13 is a cross-sectional view schematically illustrating a display device 1 according to another alternative embodiment. FIG. 14 is an enlarged view of a portion C of the display device 1 in FIG. 13. FIG. 13 is a cross-sectional view of the display device 1 in FIG. 1A, taken along line A-A'. In FIGS. 13 and 14, the same or like reference numerals as those of FIG. 2 denote the same or like elements, and thus, any repetitive detailed descriptions thereof will be omitted or simplified.

Referring to FIGS. 13 and 14, an embodiment of the display device 1 may include a display panel 10, a lower cover 40, an upper cover 50, and an adhesive layer 60.

The display panel 10 may include an upper surface 10US and a lower surface 10LS. In an embodiment, the lower surface 10LS of the display panel 10 may be a surface opposite to the upper surface 10US of the display panel 10. In an embodiment, the lower cover 40 may be disposed on the lower surface 10LS of the display panel 10. The upper cover 50 may be disposed on the upper surface 10US of the display panel 10.

The display panel 10 may include a sensor area SA and a display area DA. The sensor area SA may include an area exposed to a target material. The display panel 10 may display an image in the display area DA.

The display panel 10 may include a through portion TP. The through portion TP may be defined through the display panel 10 from the upper surface 10US to the lower surface 10LS. The through portion TP may include a first through portion TP1 and a second through portion TP2. The first through portion TP1 may overlap the sensor area SA.

The display panel 10 may include a substrate 100, a display layer 200, an encapsulation layer 300, and a sensor circuit layer SCL. The display layer 200 may include a pixel circuit layer 210 and a display element layer 220. In an alternative embodiment, the first display element DPE1 overlapping the sensor area SA may be omitted.

The sensor circuit layer SCL may overlap the sensor area SA. The sensor circuit layer SCL may be disposed on the substrate 100. The sensor circuit layer SCL may be exposed to the target material through the first through portion TP1.

The sensor circuit layer SCL may sense the target material. In an embodiment, the sensor circuit layer SCL may include a sensor thin-film transistor STFT that varies in resistance when exposed to the target material. The sensor thin-film transistor STFT may be electrically connected to a controller (not shown). The sensor thin-film transistor STFT may include a sensor semiconductor layer SAct, a sensor gate electrode SGE, a sensor source electrode SSE, and a sensor drain electrode SDE.

In an embodiment, the sensor gate electrode SGE may be disposed on the substrate 100. The sensor gate electrode SGE may include Al, Pt, Pd, Ag, Mg, Au, Ni, Nd, Ir, Cr, Ca, Mo, Ti, W, and/or Cu. In an embodiment, the sensor gate electrode SGE may include a single layer or a multi-layer, each layer including at least one selected from the above-described materials.

A buffer layer 111-1 may cover the sensor gate electrode SGE. The buffer layer 111-1 may include an inorganic insulating material such as $SiN_x$, SiON, and $SiO_2$, and may include a single layer or a multi-layer, each layer including at least one selected from the above-described inorganic insulating materials. In an alternative embodiment, the buffer layer 111-1 may include an organic insulating material, or may include an inorganic insulating material and an organic insulating material.

The sensor semiconductor layer SAct may be disposed on the buffer layer 111-1. The sensor semiconductor layer SAct may overlap the sensor gate electrode SGE. In an embodiment, the sensor semiconductor layer SAct may include polysilicon. In an embodiment, the sensor semiconductor layer SAct may include amorphous silicon, an oxide semiconductor, or an organic semiconductor. The sensor semiconductor layer SAct may include a channel area, and a drain area and a source area respectively arranged at opposite sides of the channel area.

An M13 bacteriophage VNP may be disposed on the sensor semiconductor layer SAct. In an embodiment, the M13 bacteriophage VNP may be patterned in the sensor semiconductor layer SAct.

The sensor source electrode SSE and the sensor drain electrode SDE may be arranged at opposite ends of the sensor semiconductor layer SAct, respectively. In an embodiment, the sensor source electrode SSE may at least partially overlap the source area of the sensor semiconductor layer SAct. The sensor drain electrode SDE may at least partially overlap the drain area of the sensor semiconductor layer SAct.

In an embodiment, the sensor source electrode SSE and the sensor drain electrode SDE may include a material having high conductivity. At least one selected from the sensor source electrode SSE and the sensor drain electrode SDE may include a conductive material including Mo, Al, Cu, Ti, or the like, and may include a single layer or a multi-layer, each layer including at least one selected from the above-mentioned conductive materials. In an embodiment, at least one selected from the sensor source electrode SSE and the sensor drain electrode SDE may have a multi-layer structure of a Ti layer, an Al layer, and another Ti layer.

In an embodiment of the display device 1, the display panel 10 has the through portion TP, and thus, a shape of the display device 1 may be changed relatively freely. Thus, the display device 1 may be deformed according to a shape of a user's skin and attached to the user's skin.

In an embodiment of the display device 1, a target material may pass through the first through portion TP1 of the display device 1 and reach the sensor circuit layer SCL. When the target material reaches the sensor circuit layer SCL, a resistance of the sensor thin-film transistor STFT included in the sensor circuit layer SCL may vary. In such an embodiment, a current flowing in the sensor thin-film transistor STFT may vary. In this case, the sensor circuit layer SCL may obtain information on a change in resistance and/or current, and the controller (not shown) may detect the change in resistance and/or current and determine whether the target material is present. In such an embodiment, the controller may control the display panel 10 to display a diagnosis result in the display area DA. As described above, in an embodiment of the display device 1 of the present disclosure, a system for detecting a target material may be simplified.

As described above, embodiments of a display device according to the invention may detect a target material and diagnose various illnesses. In such embodiments, a display device may display a detection result.

The invention should not be construed as being limited to the embodiments set forth herein. Rather, these embodiments are provided so that this disclosure will be thorough and complete and will fully convey the concept of the invention to those skilled in the art.

While the invention has been particularly shown and described with reference to embodiments thereof, it will be understood by those of ordinary skill in the art that various changes in form and details may be made therein without departing from the spirit or scope of the invention as defined by the following claims.

What is claimed is:

1. A display device comprising:
a display panel including a sensor area and a display area, wherein the display panel includes an upper surface and a lower surface opposite to the upper surface;
a discoloration sensor layer overlapping the sensor area, wherein the discoloration sensor layer is disposed on one of the upper surface of the display panel and the lower surface of the display panel, and discolored when exposed to a target material; and
a light detection layer comprising a photodiode,
wherein a first through portion is defined through the display panel from the upper surface to the lower surface of the display panel, and
the discoloration sensor layer is disposed between the light detection layer and the display panel, and overlaps the first through portion.

2. The display device of claim 1, wherein the discoloration sensor layer includes M13 bacteriophage.

3. The display device of claim 1,
wherein the light detection layer further comprises a color filter disposed on the photodiode, and
the color filter is arranged between the display panel and the photodiode.

4. The display device of claim 1, further comprising:
a lower cover facing the lower surface of the display panel, wherein a lower hole is defined in the lower cover to overlap the first through portion,
wherein the lower hole exposes the discoloration sensor layer.

5. The display device of claim 4, wherein the lower cover includes an elastomer.

6. The display device of claim 4, wherein the discoloration sensor layer faces the upper surface of the display panel.

7. The display device of claim 4, wherein the discoloration sensor layer is arranged between the display panel and the lower cover.

8. The display device of claim 7, wherein
the display panel comprises a substrate, a display layer disposed on the substrate, and a light reflection layer disposed on the display layer, and
the light reflection layer overlaps the sensor area.

9. The display device of claim 1, wherein the display panel further comprises:
a substrate; and
a display layer disposed on the substrate, wherein the display layer comprises a first display element overlapping the sensor area and a second display element overlapping the display area.

10. The display device of claim 1, wherein
a second through portion is defined through the display panel from the upper surface and the lower surface, and
the second through portion overlaps the display area.

11. A display device comprising:
a display panel including a sensor area and a display area, wherein the display panel includes an upper surface and a lower surface opposite to the upper surface; and
a discoloration sensor layer comprising an M13 bacteriophage and overlapping the sensor area,
wherein a first through portion is defined through the display panel from the upper surface to the lower surface, and overlaps the sensor area, and
a second through portion is defined through the display panel from the upper surface to the lower surface, and overlaps the display area.

12. The display device of claim 11,
wherein the discoloration sensor layer is disposed on one of the upper surface of the display panel and the lower surface of the display panel, and discolored when exposed to a target material, and
wherein the M13 bacteriophage is arranged in the discoloration sensor layer.

13. The display device of claim 12, further comprising:
a light detection layer overlapping the sensor area, wherein the light detection layer comprises a photodiode and a color filter disposed on the photodiode,
wherein the discoloration sensor layer is arranged between the light detection layer and the display panel, and the color filter is arranged between the display panel and the photodiode.

14. The display device of claim 12, further comprising:
a lower cover facing the lower surface of the display panel, wherein a lower hole is defined through the lower cover to overlap the first through portion,
wherein the lower hole exposes the discoloration sensor layer.

15. The display device of claim 14, wherein the lower cover includes an elastomer.

16. The display device of claim 14, wherein the discoloration sensor layer faces the upper surface of the display panel.

17. The display device of claim 14, wherein
the discoloration sensor layer is arranged between the display panel and the lower cover,
the display panel comprises a substrate, a display layer disposed on the substrate, and a light reflection layer disposed on the display layer, and
the light reflection layer overlaps the sensor area.

18. The display device of claim 12, wherein the display panel further comprises:
a substrate; and
a display layer disposed on the substrate, wherein the display layer comprises a first display element overlapping the sensor area and a second display element overlapping the display area.

19. The display device of claim 11, wherein the display panel further comprises:
a substrate; and
a sensor circuit layer disposed on the substrate to overlap the sensor area, wherein the sensor circuit layer comprises a sensor thin-film transistor, and a resistance of the sensor thin-film transistor varies when exposed to a target material, and
the sensor thin-film transistor includes a semiconductor layer on which the M13 bacteriophage is arranged.

* * * * *